(12) United States Patent
Martin et al.

(10) Patent No.: US 11,661,574 B2
(45) Date of Patent: May 30, 2023

(54) FLUIDIC DEVICES INCLUDING MICROPLATES WITH INTERCONNECTED WELLS

(71) Applicant: CORNING INCORPORATED, Corning, NY (US)

(72) Inventors: Gregory Roger Martin, Acton, ME (US); Allison Jean Tanner, Portsmouth, NH (US)

(73) Assignee: CORNING INCORPORATED, Corning, NY (US)

( * ) Notice: Subject to any disclaimer, the term of this patent is extended or adjusted under 35 U.S.C. 154(b) by 278 days.

(21) Appl. No.: 16/630,024

(22) PCT Filed: Jul. 13, 2018

(86) PCT No.: PCT/US2018/042004
§ 371 (c)(1),
(2) Date: Jan. 10, 2020

(87) PCT Pub. No.: WO2020/013851
PCT Pub. Date: Jan. 16, 2020

(65) Prior Publication Data
US 2021/0062127 A1    Mar. 4, 2021

(51) Int. Cl.
*C12M 1/32* (2006.01)
*B01L 3/00* (2006.01)
(Continued)

(52) U.S. Cl.
CPC ......... *C12M 23/12* (2013.01); *B01L 3/50273* (2013.01); *C12M 23/38* (2013.01);
(Continued)

(58) Field of Classification Search
CPC ....... B01L 2200/027; B01L 2300/0864; B01L 2300/123; B01L 2400/0475;
(Continued)

(56) References Cited

U.S. PATENT DOCUMENTS

| 2,947,116 A | 8/1960 | Earle et al. |
| 3,630,849 A | 12/1971 | Land et al. |

(Continued)

FOREIGN PATENT DOCUMENTS

| AU | 2004256209 A1 | 1/2005 |
| CA | 2558946 A1 | 1/2005 |

(Continued)

OTHER PUBLICATIONS

McMillan, "Shear stress in microfluidic devices" Darwin Microfludics interner article (Year: 2017).*
(Continued)

*Primary Examiner* — Jennifer Wecker
*Assistant Examiner* — Jonathan Bortoli
(74) *Attorney, Agent, or Firm* — Michael G. Panian

(57) ABSTRACT

A fluidic device for culturing cells includes a microplate and plate lid. The microplate includes multiple wells and channels, the channels extending between the wells such that the channels interconnect the wells. The plate lid releasably engages the microplate to thereby enclose the wells and the channels. The wells include a culture surface such that a cell culture medium received therein is deposited over the culture surface. At least one channel that extends between adjacent ones of the wells is spaced from the culture surfaces of the adjacent wells defining a gap between the at least one channel and the culture surfaces of the adjacent wells for collection of the cell culture medium.

25 Claims, 11 Drawing Sheets

(51) Int. Cl.
   *C12M 1/00*   (2006.01)
   *C12M 1/12*   (2006.01)
(52) U.S. Cl.
   CPC ........ *C12M 25/04* (2013.01); *B01L 2200/027*
         (2013.01); *B01L 2300/0864* (2013.01); *B01L*
                *2300/123* (2013.01); *B01L 2400/0475*
                                         (2013.01)
(58) Field of Classification Search
   CPC ... B01L 3/50273; C12M 23/12; C12M 23/38;
            C12M 25/04; C12M 29/10; C12M 35/04
   See application file for complete search history.

(56) References Cited

U.S. PATENT DOCUMENTS

| | | |
|---|---|---|
| 4,382,685 A | 5/1983 | Pearson |
| 4,498,785 A | 2/1985 | de Bruyne |
| 4,534,656 A | 8/1985 | de Bruyne |
| 4,670,396 A | 6/1987 | Bear et al. |
| 4,760,028 A | 7/1988 | De Bruyne et al. |
| 4,927,764 A | 5/1990 | Lyman et al. |
| 4,980,293 A | 12/1990 | Jeffs |
| 5,047,347 A | 9/1991 | Cline |
| 5,151,366 A | 9/1992 | Serkes et al. |
| 5,171,994 A | 12/1992 | Bahraman |
| 5,171,995 A | 12/1992 | Gast et al. |
| 5,240,854 A | 8/1993 | Berry et al. |
| 5,272,084 A | 12/1993 | O'Connell et al. |
| 5,319,436 A | 6/1994 | Manns et al. |
| 5,374,557 A | 12/1994 | Verma |
| 5,398,837 A | 3/1995 | Degrassi |
| 5,487,872 A | 1/1996 | Hafeman et al. |
| 5,554,536 A | 9/1996 | Rising |
| 5,598,262 A | 1/1997 | Jutard et al. |
| 5,665,562 A | 9/1997 | Cook |
| 5,693,537 A | 12/1997 | Wilson et al. |
| 5,707,869 A | 1/1998 | Wolf et al. |
| 5,710,043 A | 1/1998 | Pay |
| 5,736,397 A | 4/1998 | Garcia et al. |
| 5,759,494 A | 6/1998 | Szlosek |
| 5,766,949 A | 6/1998 | Liau et al. |
| 5,772,905 A | 6/1998 | Chou |
| 5,783,440 A | 7/1998 | Stevens |
| 5,792,653 A | 8/1998 | Weibezahn et al. |
| 5,858,309 A | 1/1999 | Mathus et al. |
| 5,972,694 A | 10/1999 | Mathus |
| 6,030,829 A | 2/2000 | Dannoux et al. |
| 6,039,972 A | 3/2000 | Barlow et al. |
| 6,306,646 B1 | 10/2001 | Saad et al. |
| 6,348,999 B1 | 2/2002 | Summersgill et al. |
| 6,514,464 B1 | 2/2003 | Knebel |
| 6,521,451 B2 | 2/2003 | Potter |
| 6,567,675 B1 | 5/2003 | Rosen et al. |
| 6,767,607 B2 | 7/2004 | Tanner et al. |
| 6,811,752 B2 | 11/2004 | Barbera-Guillem |
| 6,908,767 B2 | 6/2005 | Bader |
| 7,470,424 B2 | 12/2008 | Kataoka et al. |
| 7,547,547 B2 | 6/2009 | Dang et al. |
| 7,674,346 B2 | 3/2010 | Clements et al. |
| 7,687,262 B2 | 3/2010 | Cattadoris |
| 7,691,369 B2 | 4/2010 | Kataoka et al. |
| 7,727,759 B2 | 6/2010 | Ozawa et al. |
| 7,745,209 B2 | 6/2010 | Martin et al. |
| 7,745,210 B2 | 6/2010 | Martin |
| 7,897,379 B2 | 3/2011 | Kenney et al. |
| 7,919,319 B2 | 4/2011 | Jervis et al. |
| 8,053,230 B2 | 11/2011 | Whittlinger |
| 8,143,053 B2 | 3/2012 | Yerbic |
| 8,148,152 B2 | 4/2012 | Kolossov et al. |
| 8,158,426 B2 | 4/2012 | Wilson et al. |
| 8,158,427 B2 | 4/2012 | Wilson et al. |
| 8,163,537 B2 | 4/2012 | Martin et al. |
| 8,168,432 B2 | 5/2012 | Wilson et al. |
| 8,178,345 B2 | 5/2012 | Bennett et al. |
| 8,273,572 B2 | 9/2012 | Martin et al. |
| 8,318,479 B2 | 11/2012 | Domansky et al. |
| 8,415,144 B2 | 4/2013 | Wilson et al. |
| 8,470,589 B2 | 6/2013 | Martin et al. |
| D685,497 S | 7/2013 | Kenney et al. |
| 8,486,692 B2 | 7/2013 | Simon |
| 8,597,597 B2 | 12/2013 | Deutsch et al. |
| 8,617,879 B2 | 12/2013 | Yu et al. |
| 8,697,443 B2 | 4/2014 | Wilson et al. |
| 8,759,017 B2 | 6/2014 | Owen et al. |
| 8,778,669 B2 | 7/2014 | Lacey et al. |
| 8,846,399 B2 | 9/2014 | Martin et al. |
| 8,906,685 B2 | 12/2014 | Takayama et al. |
| 8,932,544 B2 | 1/2015 | Mueller et al. |
| 9,039,883 B2 | 5/2015 | Guerrieri et al. |
| 9,040,293 B2 | 5/2015 | Gulzow et al. |
| 9,045,721 B2 | 6/2015 | Martin et al. |
| 9,068,281 B2 | 6/2015 | Wu et al. |
| 9,126,199 B2 | 9/2015 | Moritz et al. |
| 9,169,460 B2 | 10/2015 | Cecchi |
| D748,812 S | 2/2016 | Kenney et al. |
| 9,260,684 B1 | 2/2016 | Egeler et al. |
| 9,260,695 B2 | 2/2016 | Crowley et al. |
| 9,493,733 B2 | 11/2016 | Giles |
| 9,494,577 B2 | 11/2016 | McGarr et al. |
| 9,573,128 B1 | 2/2017 | McClelland |
| 9,587,213 B2 | 3/2017 | Morgan et al. |
| 9,732,317 B2 | 8/2017 | Wilson |
| 9,790,465 B2 | 10/2017 | Bennett et al. |
| 9,845,451 B2 | 12/2017 | Martin et al. |
| 9,862,918 B2 | 1/2018 | Ito |
| 10,254,274 B2 | 4/2019 | Miklas et al. |
| 11,441,121 B2 | 9/2022 | Bennett et al. |
| 2002/0022219 A1 | 2/2002 | Clements et al. |
| 2002/0172621 A1* | 11/2002 | Barbera-Guillem ........................ B01L 3/50853 422/503 |
| 2003/0031829 A1 | 2/2003 | Tanner et al. |
| 2003/0104494 A1 | 6/2003 | Ravkin et al. |
| 2003/0183958 A1 | 10/2003 | Goff et al. |
| 2003/0186217 A1 | 10/2003 | Bader |
| 2003/0215941 A1 | 11/2003 | Campbell et al. |
| 2004/0091397 A1 | 5/2004 | Picard |
| 2004/0101955 A1 | 5/2004 | Whitley |
| 2004/0125266 A1 | 7/2004 | Miyauchi et al. |
| 2004/0216835 A1 | 11/2004 | Tanner et al. |
| 2004/0259242 A1 | 12/2004 | Malinge et al. |
| 2004/0259423 A1 | 12/2004 | Elbaz et al. |
| 2005/0032208 A1 | 2/2005 | Oh et al. |
| 2005/0047971 A1 | 3/2005 | Clements et al. |
| 2005/0074873 A1 | 4/2005 | Shanler et al. |
| 2005/0112030 A1 | 5/2005 | Gaus |
| 2005/0116717 A1 | 6/2005 | Dransfield et al. |
| 2005/0147959 A1 | 7/2005 | Frondoza et al. |
| 2006/0110822 A1 | 5/2006 | Robbins et al. |
| 2006/0234370 A1 | 10/2006 | Korpinen et al. |
| 2006/0252044 A1 | 11/2006 | Okumura et al. |
| 2006/0292654 A1 | 12/2006 | Reardon |
| 2007/0178441 A1 | 8/2007 | Li |
| 2007/0216897 A1 | 9/2007 | Sonda |
| 2008/0003671 A1 | 1/2008 | Martin |
| 2008/0009027 A1 | 1/2008 | Fraker et al. |
| 2008/0118974 A1 | 5/2008 | Martin et al. |
| 2008/0206857 A1 | 8/2008 | Kenney et al. |
| 2008/0268515 A1 | 10/2008 | Cullimore et al. |
| 2008/0297784 A1 | 12/2008 | Leblanc et al. |
| 2008/0299649 A1 | 12/2008 | Martin et al. |
| 2008/0300278 A1 | 12/2008 | Torrens et al. |
| 2009/0017540 A1 | 1/2009 | Nishio et al. |
| 2009/0018033 A1 | 1/2009 | Morgan et al. |
| 2009/0029462 A1 | 1/2009 | Beardsley et al. |
| 2009/0037293 A1 | 2/2009 | Unger et al. |
| 2009/0170190 A1 | 7/2009 | Nishi et al. |
| 2009/0191620 A1 | 7/2009 | Martin et al. |
| 2009/0288963 A1 | 11/2009 | Guerrieri et al. |
| 2009/0298164 A1 | 12/2009 | Cattadoris et al. |
| 2009/0298166 A1 | 12/2009 | Fang et al. |
| 2010/0055774 A1 | 3/2010 | Wilson |
| 2010/0068793 A1 | 3/2010 | Ungrin et al. |

(56) References Cited

U.S. PATENT DOCUMENTS

| | | | |
|---|---|---|---|
| 2010/0093075 | A1 | 4/2010 | Muller |
| 2010/0112014 | A1 | 5/2010 | Gilbert et al. |
| 2010/0112684 | A1 | 5/2010 | Lee et al. |
| 2010/0119418 | A1 | 5/2010 | Clements et al. |
| 2010/0170790 | A1 | 7/2010 | Takahashi et al. |
| 2010/0190197 | A1 | 7/2010 | Martin et al. |
| 2010/0197013 | A1 | 8/2010 | Kamp et al. |
| 2010/0247386 | A1 | 9/2010 | Deutsch et al. |
| 2010/0273258 | A1 | 10/2010 | Lannutti et al. |
| 2010/0297600 | A1 | 11/2010 | Cecchi |
| 2011/0086375 | A1 | 4/2011 | Ungrin et al. |
| 2011/0097790 | A1 | 4/2011 | Yerbic |
| 2011/0129923 | A1 | 6/2011 | Wilson et al. |
| 2011/0229961 | A1* | 9/2011 | Higashi ............... C12M 29/10 435/287.1 |
| 2012/0064627 | A1 | 3/2012 | Khine et al. |
| 2012/0129208 | A1 | 5/2012 | Khine et al. |
| 2012/0129257 | A1 | 5/2012 | Yu et al. |
| 2012/0219572 | A1 | 8/2012 | Prockop et al. |
| 2013/0052331 | A1 | 2/2013 | Kram et al. |
| 2013/0122539 | A1 | 5/2013 | Li et al. |
| 2013/0122580 | A1 | 5/2013 | Tsukada et al. |
| 2013/0143254 | A1 | 6/2013 | Thomas et al. |
| 2013/0164848 | A1 | 6/2013 | Naka et al. |
| 2013/0203159 | A1 | 8/2013 | Itoh et al. |
| 2013/0344598 | A1 | 12/2013 | Nistor |
| 2014/0004086 | A1 | 1/2014 | Peak |
| 2014/0027784 | A1 | 1/2014 | Wada et al. |
| 2014/0099717 | A1 | 4/2014 | Fraker et al. |
| 2014/0106394 | A1 | 4/2014 | Ko et al. |
| 2014/0106452 | A1 | 4/2014 | Vukasinovic |
| 2014/0120573 | A1 | 5/2014 | Tavana et al. |
| 2014/0178992 | A1 | 6/2014 | Nakashima et al. |
| 2014/0221225 | A1 | 8/2014 | Danen et al. |
| 2014/0226004 | A1 | 8/2014 | Son et al. |
| 2014/0227784 | A1 | 8/2014 | Ejiri et al. |
| 2014/0315296 | A1 | 10/2014 | Wilson |
| 2014/0322806 | A1 | 10/2014 | Bennett et al. |
| 2015/0004686 | A1 | 1/2015 | Goral et al. |
| 2015/0064738 | A1 | 3/2015 | Tsukada et al. |
| 2015/0072405 | A1 | 3/2015 | Ito |
| 2015/0184119 | A1 | 7/2015 | Tsukada et al. |
| 2015/0247112 | A1 | 9/2015 | Orr et al. |
| 2016/0003796 | A1 | 1/2016 | Kranbuehl |
| 2016/0017267 | A1 | 1/2016 | Hansen et al. |
| 2016/0040120 | A1* | 2/2016 | Gottwald ............ C12N 5/0647 435/395 |
| 2016/0137962 | A1 | 5/2016 | Ejiri et al. |
| 2016/0194588 | A1 | 7/2016 | Guenat et al. |
| 2016/0216250 | A1 | 7/2016 | Ritter et al. |
| 2017/0067019 | A1 | 3/2017 | Ho |
| 2017/0073625 | A1 | 3/2017 | Kasuto et al. |
| 2017/0226455 | A1 | 8/2017 | Fang et al. |
| 2017/0267959 | A1 | 9/2017 | Martin et al. |
| 2017/0283757 | A1 | 10/2017 | Carter et al. |
| 2017/0306281 | A1 | 10/2017 | Martin et al. |
| 2017/0342363 | A1 | 11/2017 | Fang et al. |
| 2018/0166743 | A1 | 6/2018 | Lee et al. |
| 2018/0201888 | A1 | 7/2018 | Miwa et al. |
| 2018/0301754 | A1 | 10/2018 | Badding et al. |
| 2019/0006707 | A1 | 1/2019 | Sakamoto et al. |
| 2020/0239854 | A1 | 7/2020 | Ayano et al. |

FOREIGN PATENT DOCUMENTS

| | | |
|---|---|---|
| CA | 2679011 A1 | 9/2008 |
| CA | 2848875 A1 | 3/2013 |
| CN | 2186755 Y | 1/1995 |
| CN | 1168921 A | 12/1997 |
| CN | 1234112 A | 11/1999 |
| CN | 1867663 A | 11/2006 |
| CN | 1875093 A | 12/2006 |
| CN | 201626959 U | 11/2010 |
| CN | 101978041 A | 2/2011 |
| CN | 102105578 A | 6/2011 |
| CN | 102257123 A | 11/2011 |
| CN | 102449135 A | 5/2012 |
| CN | 102687023 A | 9/2012 |
| CN | 202450098 U | 9/2012 |
| CN | 202849407 U | 4/2013 |
| CN | 103080294 A | 5/2013 |
| CN | 103119151 A | 5/2013 |
| CN | 203513696 U | 4/2014 |
| CN | 103814125 A | 5/2014 |
| CN | 204608026 U | 9/2015 |
| CN | 204702760 U | 10/2015 |
| CN | 204714819 U | 10/2015 |
| CN | 204752742 U | 11/2015 |
| CN | 204803327 U | 11/2015 |
| CN | 205170866 U | 4/2016 |
| CN | 205669029 U | 11/2016 |
| CN | 205839030 U | 12/2016 |
| CN | 205990396 U | 3/2017 |
| CN | 107208025 A | 9/2017 |
| CN | 107460125 A | 12/2017 |
| DE | 8309876 U1 | 12/1983 |
| DE | 10019862 A1 | 11/2001 |
| DE | 202006017853 U1 | 2/2007 |
| DE | 102009005526 A1 | 7/2010 |
| DE | 102014214077 A1 | 1/2016 |
| DE | 102014017728 A1 | 6/2016 |
| EP | 307048 A2 | 3/1989 |
| EP | 0605527 A1 | 7/1994 |
| EP | 0681846 A2 | 11/1995 |
| EP | 0800571 A2 | 10/1997 |
| EP | 834552 A1 | 4/1998 |
| EP | 965633 A1 | 12/1999 |
| EP | 1181349 A1 | 2/2002 |
| EP | 1348533 A2 | 10/2003 |
| EP | 1445022 A2 | 8/2004 |
| EP | 1988152 A1 | 11/2008 |
| EP | 2032262 A2 | 3/2009 |
| EP | 2617807 A1 | 7/2013 |
| EP | 2653531 A1 | 10/2013 |
| EP | 2759592 A1 | 7/2014 |
| EP | 2896684 A1 | 7/2015 |
| EP | 3081627 A1 | 10/2016 |
| EP | 3296018 A1 | 3/2018 |
| EP | 3351615 A1 | 7/2018 |
| EP | 3372666 A1 | 9/2018 |
| GB | 2147100 A | 5/1985 |
| JP | 03-139350 A | 6/1991 |
| JP | 06-038734 A | 2/1994 |
| JP | 06327462 A | 11/1994 |
| JP | 09173049 A | 7/1997 |
| JP | 09-234811 A | 9/1997 |
| JP | 10210866 A | 8/1998 |
| JP | 10210966 A | 8/1998 |
| JP | 2001-106749 A | 4/2001 |
| JP | 2003135056 A | 5/2003 |
| JP | 2003180335 A | 7/2003 |
| JP | 2004129558 A | 4/2004 |
| JP | 2004-535829 A | 12/2004 |
| JP | 2005-080660 A | 3/2005 |
| JP | 2006-121991 A | 5/2006 |
| JP | 2006-191809 A | 7/2006 |
| JP | 2007-510429 A | 4/2007 |
| JP | 3139350 U | 2/2008 |
| JP | 2009-017810 A | 1/2009 |
| JP | 2009050194 A | 3/2009 |
| JP | 2009-183288 A | 8/2009 |
| JP | 2009-542230 A | 12/2009 |
| JP | 2010088347 A | 4/2010 |
| JP | 2010104327 A | 5/2010 |
| JP | 2010-518879 A | 6/2010 |
| JP | 2010158214 A | 7/2010 |
| JP | 2011-509686 A | 3/2011 |
| JP | 2011-521642 A | 7/2011 |
| JP | 2011172533 A | 9/2011 |
| JP | 2011-528226 A | 11/2011 |
| JP | 2012249547 A | 12/2012 |
| JP | 2013055911 A | 3/2013 |
| JP | 2014132869 A | 7/2014 |

(56) References Cited

FOREIGN PATENT DOCUMENTS

| | | |
|---|---|---|
| JP | 2015012827 A | 1/2015 |
| JP | 2015-029431 A | 2/2015 |
| JP | 2015073520 A | 4/2015 |
| JP | 2016-002023 A | 1/2016 |
| JP | 5845185 B2 | 1/2016 |
| JP | 2016-093149 A | 5/2016 |
| JP | 2016-136920 A | 8/2016 |
| JP | 2016136921 A | 8/2016 |
| JP | 2017-532970 A | 11/2017 |
| JP | 2018-108032 A | 7/2018 |
| KR | 1020140113139 A | 9/2014 |
| KR | 10-2014-0125662 A | 10/2014 |
| KR | 10-2017-0008539 A | 1/2017 |
| WO | 1992007063 A2 | 4/1992 |
| WO | 93/07258 A1 | 4/1993 |
| WO | 96/21851 A2 | 7/1996 |
| WO | 9815355 A2 | 4/1998 |
| WO | 1998031466 A1 | 7/1998 |
| WO | 2001080997 A1 | 11/2001 |
| WO | 2001092462 A1 | 12/2001 |
| WO | 2004/044120 A2 | 5/2004 |
| WO | 2004/094060 A1 | 11/2004 |
| WO | 2005047464 A2 | 5/2005 |
| WO | 2006043267 A1 | 4/2006 |
| WO | 2007/015770 A1 | 2/2007 |
| WO | 2007097120 A1 | 8/2007 |
| WO | 2008/006104 A2 | 1/2008 |
| WO | 2008/008149 A2 | 1/2008 |
| WO | 2008/106771 A1 | 9/2008 |
| WO | 2008118500 A1 | 10/2008 |
| WO | 2008/140295 A1 | 11/2008 |
| WO | 2008153783 A1 | 12/2008 |
| WO | WO-2008149039 A2 * | 12/2008 ............ C12M 23/12 |
| WO | 2009094125 A2 | 7/2009 |
| WO | 2009148509 A1 | 12/2009 |
| WO | 2009148512 A2 | 12/2009 |
| WO | 2010008566 A2 | 1/2010 |
| WO | 2010/042072 A1 | 4/2010 |
| WO | 2010/069589 A1 | 6/2010 |
| WO | 2012036011 A1 | 3/2012 |
| WO | 2012/077683 A1 | 6/2012 |
| WO | 2012170232 A1 | 12/2012 |
| WO | 2013042360 A1 | 3/2013 |
| WO | 2013/108293 A1 | 7/2013 |
| WO | 2013/116449 A1 | 8/2013 |
| WO | 2014/042162 A1 | 3/2014 |
| WO | 2014072432 A1 | 5/2014 |
| WO | 2014/140181 A1 | 9/2014 |
| WO | 2014156455 A1 | 10/2014 |
| WO | 2014165273 A1 | 10/2014 |
| WO | 2014171782 A1 | 10/2014 |
| WO | 2014/179196 A1 | 11/2014 |
| WO | 2014196204 A1 | 12/2014 |
| WO | 2015033507 A1 | 3/2015 |
| WO | 2015/061907 A1 | 5/2015 |
| WO | 2015/087369 A1 | 6/2015 |
| WO | 2016/020992 A1 | 2/2016 |
| WO | 2016064757 A1 | 4/2016 |
| WO | 2016069885 A1 | 5/2016 |
| WO | 2016069892 A1 | 5/2016 |
| WO | 2016069895 A1 | 5/2016 |
| WO | 2016069917 A1 | 5/2016 |
| WO | 2016069930 A1 | 5/2016 |
| WO | 2016/157322 A1 | 10/2016 |
| WO | 2017025584 A1 | 2/2017 |
| WO | 2017/047735 A1 | 3/2017 |
| WO | 2017/077163 A1 | 5/2017 |
| WO | WO-2017077163 A1 * | 5/2017 ............ B01L 3/5027 |
| WO | 2017142410 A1 | 8/2017 |
| WO | 2018/068034 A1 | 4/2018 |
| WO | 2018200893 A1 | 11/2018 |
| WO | 2019014621 A1 | 1/2019 |
| WO | 2019014627 A1 | 1/2019 |
| WO | 2019014635 A1 | 1/2019 |
| WO | 2019014636 A1 | 1/2019 |
| WO | 2019178039 A1 | 9/2019 |

OTHER PUBLICATIONS

WO-2008149039 translation (Year: 2008).*
WO 2017/077163 (Year: 2017).*
International Search Report and Written Opinion of the International Searching Authority; PCT/US2018/042004; dated Apr. 4, 2019; 10 Pages; European Patent Office.
Lovett et al. "Vascularization Strategies for Tissue Engineering" Tissue Engineering Part B, 2009, vol. 15, No. 3, pp. 353-370.
Office Action dated Aug. 8, 2019 pertaining to U.S. Appl. No. 15/708,473, filed Sep. 19, 2017, 20 pgs.
Moon et al, "Optimizing Human Embryonic Stem Cells Differentiation Efficiency by Screening Size-Tunable Homogenous Embryoid Bodies" ; Biomaterials; 35 (2014) 5987-5997.
Urich et al, "Multicellular Self-Assembled Spheroidal Model of the Blood Brain Barrier"; Scientific Reports, 3, 1500, 8 Pages.
Murphy et al, "3D Bioprinting of Tissues and Organs" ; Nature Biotechnology, vol. 32, No. 8, Aug. 2014, pp. 773-785.
Nortis; "Bridging the Gap Between in Vitro and in Vivo Research"; 16 Pages; (2015); https://www.nortisbio.com/.
Mimetas the Organ-on-a-Chip Company; "Organ-on-a-Chip Models for Science and Pharma"; 4 Pages; (Downloaded Mar. 9, 2020); https://mimetas.com/.
Otsuka et al, "Two-dimensional multiarray formation of hepatocyte spheroids on a microfabricated PEG-brush surface." ChemBioChem 2004; 5:850-855.
Peshwa et al, "Mechanistics of formation and ultrastructural evaluation of hepatocyte spheroids." In Vitro Cell Dev Biol Anim 1996; 32:197-203.
Organovo, "Pioneering Bioprinted Tissues to Treat Disease"; 2 Pages; (Downloaded Mar. 9, 2020) http://organovo.com/.
Rezende et al, "Scalable Biofabrication of Tissue Spheroids for Organ Printing"; Sciverse Science Direct, Procedia Cirp 5, (2013) 276-281.
Sa et al, "Round-bottomed Honeycomb Microwells: Embryoid body shape correlates with stem cell fate" Journal of Developmental Biology and Tissue Engineering vol. 4(2), pp. 12-22, May 2012.
Sakai et al, "Large-scale preparation and function of porcine hepatocyte spheroids." Int J Artif Organs 1996; vol. 19, No. 5, pp. 294-301.
Sakai et al, "Detachably Assembled Microfluidic Device for Perfusion Culture and Post-Culture Analysis of Spheroid Array" ; Biotechnol. J. 2014, 9, 971-979.
Sakai et al, "Technique for the Control of Spheroid Diameter Using Microfabricated Chips"; Sciencedirect, Acta Biomaterialia 3 (2007) 1033-1040.
Sart et al, "Three-dimensional aggregates of mesenchymal stem cells: cellular mechanisms, biological properties and applications" Tissue engineering, 2013, Part B, vol. 00, No. 00, 1-16.
Satoh et al, "A Pneumatic Pressure-Driven Multi-Throughput Microfluidic Circulation Culture System" Lab Chip, 2016, 16, 2339-2348.
Seldon et al, "Evaluation of Encapsulated Liver Cell Spheroids in a Fluidised-Bed Bioartificial Liver for Treatment of Ischaemic Acute Liver Failure in Pigs in a Translational Setting"; PLoS One, 2013, 8(12), e82312.
Takezawa et al, "Morphological and immuno-cytochemical characterization of a hetero-spheroid composed of fibroblasts and hepatocytes" J Cell Sci 1992; 101:495-501.
Tara; "Innovating Predictive Cardiac Physiology" ; 4 Pages; (2019) http://tarabiosystems.com/.
The Lab Depot® Products for Discovery Lab Supplies; Shake Flasks, 3 and 4 Baffles Product Information; 5 Pages (2019).
Tobe et al, "Receptor-mediated formation of multilayer aggregates of primary cultured adult rat hepatocytes on lactose-substituted polystyrene" Biochem Biophys Res Commun 1992; 184(1):225-230.
Tong et al, "Long-term culture of adult rat hepatocyte spheroids." Exp Cell Res 1992; 200:326-332.

(56) References Cited

OTHER PUBLICATIONS

Truckenmuller et al, Thermoforming of Film-Based Biomedical Microdevices, Adv. Mater. 2011, 23, pp. 1311-1329.
Tung et al, "High-throughput 3D spheroid culture and drug testing using 384 hanging drop array" Analyst, 2011, 136(3), 473-478.
Uchida et al, "An Injectable Spheroid System With Genetic Modification for Cell Transplantation Therapy"; Biomaterials, 35 (2014) 2499-2506.
Vinci et al, Advances in establishment and analysis of three-dimensional tumor spheroid-based functional assays for target validation and drug evaluation, BMC Biology 2012, 10:29.
Weegman et al, "Nutrient Regulation by Continuous Feeding Removes Limitations on Cell Yield in the Large-Scale Expansion of Mammalian Cell Spheroids"; PLoS One, 2013, vol. 8, Isuue 10, e76611, 10 Pages.
Wikipedia, "Antiroll Tanks"; 3 Pages; Page Last Edited May 23, 2019.
Wrighton et al, "Forces of Change: Mechanics Underlying Formation of Functional 3D Organ Buds" Cell Stem Cell, May 7, 2015; 16(5): 453-454.
Xu et al, "Characterisation of some cytotoxic endpoints using rat liver and HepG2 spheroids as in vitro models and their application in hepatotoxicity studies. I. Glucose metabolism and enzyme release as cytotoxic markers." Toxicol Appl Pharmacol 2003;189:100-111.
Yamada et al, "Efficient induction of hepatocyte spheroids in a suspension culture using a water-soluble synthetic polymer as an artificial matrix." J Biochem 1998; 123:1017-1023.
AxoSIM, Nerve-on-a-Chip Mini-Brain About Team; 6 Pages; (Downloaded Mar. 9, 2020); http://axosim.com/.
Corning Life Sciences Product Portfolio; 5 Pages Saved Mar. 6, 2020.
Madoux et al, "Building Phenotypic 3D Spheroid HTS Assays to Identify Synthetic Lethal Small Molecule Inhibitors of KRAS"; the Scripps Research Institute Molecular Screening Center and Department of Cancer Biology, Scripps Florida, Jupiter, Florida, Department of Pathology, Jupiter Medical Center, Jupiter, Florida.
Stemcell Technologies, Reproducible and Uniform Embryoid Bodies Using AggreWell Plates, StemCell Technologies, Technical Manual Version 3.0.0, Mar. 2011, Catalog #29146, pp. 1-28.
Achilli et al, "Advances in the Formation, Use and Understanding of Multi-Cellular Spheroids", Expert Opin. Biol. Ther. (2012) 12(10):1347-1360.
Alepee et al, "State-of-the-Art 3D Cultures (Organs-on-a-Chip) in Safety Testing and Pathophysiology"; Transatlantic Think Tank for Toxicology, T4 Workshop Report, Altex 31, 4/14, pp. 441-477, Retrieved From: http://dx.doi.org/10.14573/altex1406111 (Jul. 14, 2014).
Aline, "We Engineer Microfluidic Products"; 7 Pages; (2020) https://alineinc.com/.
G-Plate: Accelerate your cell cultures to the next dimension, "An original cell culture model allowing for island-shaped 3D cell aggregates", 1 page, retrieved Sep. 8, 2015.
Anada et al, "An Oxygen-Permeable Spheroid Culture System for the Prevention of Central Hypoxia and Necrosis of Spheroids"; Biomaterials 33 (2012) 8430-8441.
Bartosh et al, "Aggregation of Human Mesenchymal Stromal Cells (MSCS) Into 3D Spheroids Enhances Their Antiinflammatory Properties"; PNAS, Aug. 3, 2010, 107(31):13724-13729.
Bioivt Elevating Science®; 6 Pages; (2020); http://www.hepregen.com/.
Carver et al, "Multicellular Tumor Spheroids as a Model for Assessing Delivery of Oligonucleotides in Three Dimensions"; Molecular Therapy-Nucleic Acids (2014) 3, E153; 8 Pages.
Chen et al, "Microfluidic array for three-dimensional perfusion culture of human mammary epithelial cells"; Biomedical Microdevices, 2011, 13(4):753-758.
Cheng et al, "Microrna-34a Targets Forkhead Box J2 to Modulate Differentiation of Endothelial Progenitor Cells in Response to Shear Stress", J Mol Cell Cardiol. 74 (2014) 4-12.

Choi et al, "Feasibility of a simple double-layered coculture system incorporating metabolic processes of the intestine and liver tissue: application to the analysis of benzo[a]pyrene toxicity", Toxicology in Vitro 18 (2004) 393-402.
Cn-Bio, "Transforming Drug Discovery and the Lives of Patients"; 5 Pages; (2020) http://cn-bio.com/.
Colazzo et al, "Shear Stress and VEGF Enhance Endothelial Differentiation of Human Adipose-Derived Stem Cells", Growth Factors, 2014, 32(5):139-149.
Corning® HTS Transwell®-96 Tissue Culture Systems, Permeable Supports for High Throughput Screening Applications; 2 Pages (2004).
Tissue Dynamics, "Disruptive Drug Development"; 3 Pages; (Downloaded Mar. 9, 2020); https://www.tissuedynamics.com/.
Dolznig et al, "Organotypic spheroid cultures to study tumor-stroma interaction during cancer development", Drug Discovery Today: Disease Models, 2011, 8(2-3): 113-118.
Domansky et al, "Perfused Multiwell Plate for 3D Liver Tissue Engineering", Lab Chip, 2010, 10:51-58.
Emulate, 6 Pages; (2019) https://emulatebio.com/.
Tissuse, "Emulating Human Biology, Pioneering Human-on-a-Chip Developments"; 1 Page; Downloaded Mar. 9, 2020) https://www.tissuse.com/en/.
Endo et al, "Gene transfection to spheroid culture system on micropatterned culture plate by polyplex nanomicelle: a novel platform of genetically-modified cell transplantation", Drug Deliv. and Transl. Res., 2012, 2:398-405.
Engelberg et al, "Essential operating principles for tumor spheroid growth", BMC Systems Biology 2008, 2:110, 19 pages.
Friedrich et al, "Experimental anti-tumor therapy in 3-D: spheroids—old hat or new challenge?" Int J Radiat Biol 2007, 83(11-12):849-871.
Friedrich et al, "Spheroid-based drug screen: considerations and practical approach", Nature protocols, 2009, 4(3):309-323.
Frith et al, "Dynamic three-dimensional culture methods enhance mesenchymal stem cell properties and increase therapeutic potential", Tissue engineering, 2010, 16(4):735-749.
Fukuda et al, "Efficacy of a polyurethane foam/spheroid artificial liver by using human hepatoblastoma cell line (Hep G2)", Cell Transplantation, 2003, 12:51-58.
GeoCHEM Incorporated, Product Line; https://www.geocheminc.com, 4 Pages; (2020).
Haycock, "3D cell culture: a review of current approaches and techniques", Methods Mol Biol, 2011; 695:1-15.
Hirschhaeuser et al, "Multicellular tumor spheroids: An underestimated tool is catching up again", Journal of Biotechnology 148 (2010) 3-15.
Howes et al, "3-Dimensional Culture Systems for Anti-Cancer Compound Profiling and High-Throughput Screening Reveal Increases in EGFR Inhibitor-Mediated Cytotoxicity Compared to Monolayer Culture Systems"; Plos One; Sep. 2004, 9(9), 11 Pages.
Hribar et al, "Nonlinear 3D Projection Printing of Concave Hydrogel Microstructures for Long-Term Multicellular Spheroid and Embryoid Body Culture"; Lab Chip, 2015, 15, 2412-2418.
Hwang et al, "Microwell-Mediated Control of Embryoid Body Size Regulates Embryonic Stem Cell Fate Via Differential Expression of WNT5A and WNT11"; PNAS, 2009, 106(40):16978-16983.
HμREL® Corporation, Bioanalytic Tools Company; 2 Pages; (2013); http://hurelcorp.com/.
Jeon et al, "Combined Effects of Flow-Induced Shear Stress and Micropatterned Surface Morphology on Neuronal Differentiation of Human Mesenchymal Stem Cells" J Biosci Bioeng, 2014, 117(2):242-247.
Jiang et al, "Shear Enhances Thrombopoiesis and Formation of Microparticles That Induce Megakaryocytic Differentiation of Stem Cells", Blood, Sep. 25, 2014; 124(13):2094-2103.
Kelm et al, "Method for generation of homogeneous multicellular tumor spheroids applicable to a wide variety of cell types", Biotechnology and Bioengineering 2003; 83(2):173-180.
Kim et al, "Shear Stress Induced by an Interstitial Level of Slow Flow Increases the Osteogenic Differentiation of Mesenchymal Stem Cells Through Taz Activation" PLoS One, Mar. 21, 2014; 9(3), e92427, 9 pages.

(56) References Cited

OTHER PUBLICATIONS

Koide et al, "Formation of multicellular spheroids composed of adult rat hepatocytes in dishes with positively charged surfaces and under other nonadherent environments", Exp Cell Res 1990; 186:227-235.
Kunz-Schughart et al, "The use of 3-D cultures for high-throughput screening: the multicellular spheroid model", J Biomol Screen 2004, 9(4):273-285.
Kutsuzawa et al, "Highly Robust Protein Production by Co-Culture of CHO Spheroids Layered on Feeder Cells in Serum-Free Medium"; Colloid Polym Sci (2014) 292; 839-848.
Labusca, "Scaffold free 3D culture of mesenchymal stem cells; implications for regenerative medicine", J Transplant Stem Cel Biol 2015 2(1): 8.
Landry et al, "Spheroidal aggregate culture of rat liver cells: histotypic reorganization, biomatrix deposition, and maintenance of functional activities" J Cell Biol 1985; 101:914-923.
Lau et al, "Evaluation of a Novel in Vitro CACO-2 Hepatocyte Hybrid System for Predicting in Vivo Oral Bioavailability" Drug Metabolism and Disposition, vol. 32, No. 9, pp. 937-942, 2004.
Liquid Surge Control, LLC; "The Latest in Drop-in Baffle Technology"; 2 Pages; (2019).
Liu et al, "Quasi-spherical microwells on superhydrophobic substrates for long term culture of multicellular spheroids and high throughput assays" Biomaterials 35 (2014) pp. 6060-6068.
Liu et al, "Advanced Micromachining of Concave Microwells for Long Term on-Chip Culture of Multicellular Tumor Spheroids", ACS Appl. Mater. Interfaces, 2014, 6, 8090-8097.
Lu et al, "Galactosylated PVDF membrane promotes hepatocyte attachment and functional maintenance" Biomaterials 24 (2003) 4893-4903.
Markovitz-Bishitz, "A polymer microstructure array for the formation, culturing, and high throughput drug screening of breast cancer spheroids" Biomaterials 31 (2010) 8436-8444.
Messner et al, Multi-cell type human liver microtissues for hepatotoxicity testing. Archives of Toxicology, Nov. 11, 2012, 5 pages.
Elveflow; "Microfluidics Innovation Center"; 6 Pages; (Downloaded Mar. 9, 2020); https://www.elveflow.com/.
Mironov et al, "Organ Printing: Tissue Spheroids as Buliding Blocks" Biomaterials, 2009; 30(12): 2164-2174.
"Laboratory Flasks Selection Guide: Types, Features, Applications", Engineering360, <https://www.globalspec.com/learnmore/labware_scientific_instruments/labware_consumables/laboratory_flasks#:~:text=Laboratory%20flasks%20are%20lab%20vessels,the%20opening%20at%20the%20neck.> accessed Apr. 8, 2022 (Year: 2022).
Achilli et al., "Advances in the Formation, Use and Understanding of Multi-cellular Spheroids", Expert Opinion on Biological Therapy, vol. 12, No. 10, Jul. 2012, pp. 1347-1360.

Brandrup et al., "Polymer Handbook", Fourth Edition, Wiley-Interscience Publication, , Permeability and diffusion data, 1999, 9 pages (Contributors; Preface).
Endo et al., "Gene transfection to spheroid culture system on micropatterned culture plate by polyplex nanomicelle: a novel platform of genetically-modified cell transplantation", Drug Deliv. and Transl. Res., 2012, vol. 2, p. 398-405.
Hsiao et al., "Effects of 3D Microwell Culture on Initial Fate Specification in Human Embryonic Stem Cells", Published in final edited form as AIChE J. vol. 60 No. 4, Apr. 2014, pp. 1225-1235.
Huang et al., "Preparation of dense Ta-LLZO/MgO composite Li-ion solid electrolyte: Sintering, microstructure, performance and the role of MgO", Journal of Energy Chemistry, vol. 39, 2019, pp. 8-16.
International Search Report and Written Opinion of the International Searching Authority; PCT/US2021/059622; dated May 23, 2022, 11 pages; European Patent Office.
Junji Fukuda et al., "Hepatocyte Spheroid Arrays Inside Microwells Connected With Microchannels", Biomicrofluidics 5, 2011, p. 10.
Lin et al., "La2Zr2O7 and MgO co-doped composite Li-Garnet solid electrolyte", Journal of Energy Chemistry, vol. 40, 2020, pp. 132-136.
Lonza Inc., "SeaPrep Agarose: An Ultralow Gelling, Soft Agarose", Available Online at <http://www.lonzabio.jp/catalog/pdf/pd/PD031.pdf>, 2007, pp. 1-4.
Martin et al., "Agarose and Methylcellulose Hydrogel Blends for Nerve Regeneration Applications", J. Neural Eng., vol. 5, 2008, pp. 221-231.
Polyimide: Japan Polyimide and Aromatic Polymers Study Group, 2010, pp. 364-371 Table 2.
Yang et al.,"An Agarose-Gel Based Method for Transporting Cell Lines", Current Chemical Genomics, vol. 3, Jan. 2009, pp. 50-53.
Zuidema et al., "Fabrication and Characterization of Tunable Polysaccharide Hydrogel Blends for Neural Repair", Acta Biomaterialia, vol. 7, No. 4, Apr. 2011, pp. 1634-1643.
Curcio et al. "Mass transfer and metabolic reactions in hepatocyte spheroids cultured in rotating wall gas-permeable membrane system." Biomaterials 28 (2007) 5487-5497. (Year: 2007).
Evenou et al. "Spontaneous Formation of Highly Functional Three-Dimensional Multilayer from Human Hepatoma Hep G2 Cells Cultured on an Oxygen-Permeable Polydimethylsiloxane Membrane." Tissue Engineering: Part C vol. 16, No. 2, 2010, pp. 311-318. (Year: 2010).
Koike et al. "Characterization of Embryo id Bodies of Mouse Embryonic Stem Cells Formed under Various Culture Conditions and Estimation of Differentiation Status of Such Bodies." Journal of Bioscience and Bioengineering vol. I 04, No. 4, 294-299. 2007. (Year: 2007).

\* cited by examiner

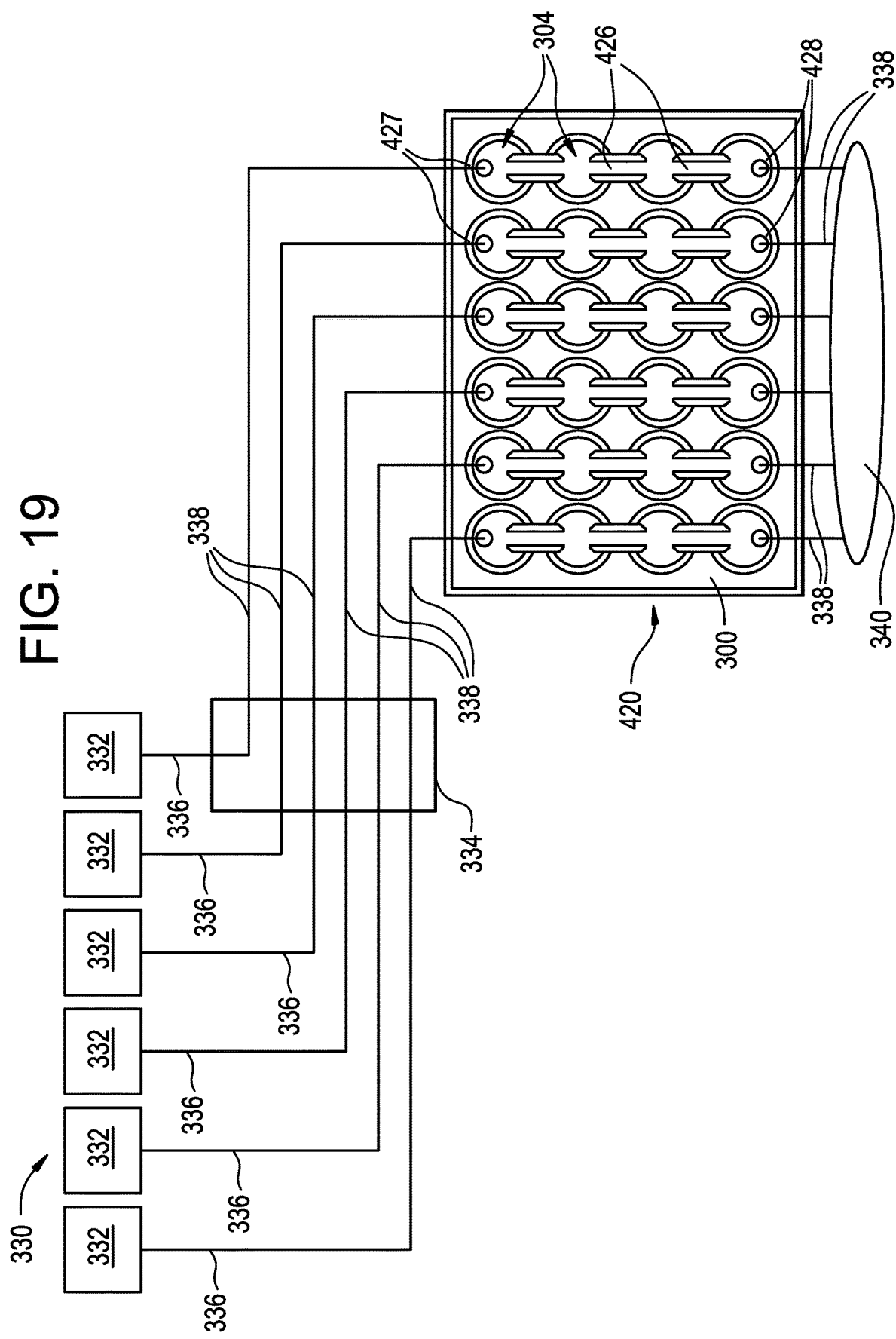

FLUIDIC DEVICES INCLUDING MICROPLATES WITH INTERCONNECTED WELLS

BACKGROUND

Field

This application claims the benefit of priority under 35 U.S.C. § 365 of International Patent Application Serial No. PCT/US2018/042004 filed on Jul. 13, 2018, the content of which is relied upon and incorporated herein by reference in its entirety.

The present specification generally relates to perfusing cell cultures to mature and differentiate the 3D cells grown therein, and more specifically, fluidic devices including microplates with interconnected wells to facilitate fluid flow between the wells.

Technical Background

Many tissues of the human body are naturally exposed to mechanical forces, including various organs, muscles, skin, etc., which are significant for the full development of such tissues. Accordingly, applying specific mechanical forces, i.e. shear stress, to cell cultures provides for desirable physiological responses to the stem cells contained therein when seeking to develop such tissues in a microplate environment. Shear stress can induce differentiation and maturation of the organoids into fully functional representations of these tissues, thereby providing an adequate simulation of the tissues for purposes of scientific research.

Generally, microfluidic cell culture plates have micron-sized fluid flow channels that require specialized equipment to operate. These devices include miniaturized constructs that seek to simulate activity of human organs at as small a scale as possible, thereby requiring constant manual intervention to ensure adequate operation. In addition to minimizing the positive effects provided by exposing stem cells to shear stress, the miniscule dimension of the fluid flow channels also impedes the ability to use such cell culture plates without specialized perfusion equipment.

Accordingly, a need exists for a microplate apparatus that incorporates relatively larger fluid flow channels for developing mature organoids within a microplate. Additionally, providing fluid flow channels with an enhanced profile enables greater automatable process control of the microplate with suitable perfusion equipment.

SUMMARY

According to one embodiment, a fluidic device for culturing cells includes a microplate comprising multiple wells and multiple channels, the channels extend between the wells such that the channels interconnect the wells. The fluidic device further includes a plate lid that releasably engages the microplate to thereby enclose the wells and the channels. The wells include a culture surface such that a cell culture medium received therein is deposited over the culture surface. At least one channel that extends between adjacent ones of the wells is spaced from the culture surfaces of the adjacent wells defining a gap between the at least one channel and the culture surfaces of the adjacent wells for collection of the cell culture medium.

According to another embodiment, a fluidic apparatus for culturing cells includes a microplate comprising multiple wells and multiple channels, wherein the channels extend between the wells such that the channels interconnect the wells, wherein the wells include a culture surface that cultivates cells therein. The fluidic apparatus includes a plate lid that releasably engages the microplate to thereby enclose the wells and the channels, wherein the plate lid includes a port that aligns with the wells in response to the plate lid engaging the microplate. The fluidic apparatus further includes an external fluid source coupled to the port such that the external fluid source transfers a cell culture medium to the wells of the microplate via the port. At least one channel that extends between adjacent ones of the wells is spaced from the culture surfaces of the adjacent wells defining a gap between the at least one channel and the culture surfaces of the adjacent wells for collection of the cell culture medium.

According to another embodiment, a method of culturing cells using a fluidic device, the method includes providing a cell culture medium to multiple wells of a microplate where the wells include a culture surface, the microplate comprising multiple channels that extend between adjacent ones of the wells, wherein at least one channel that extends between adjacent ones of the wells is spaced from the culture surfaces of the adjacent wells defining a gap between the at least one channel and the culture surfaces of the adjacent wells for collection of the cell culture medium; and introducing fluid to the wells thereby resulting in fluid flowing between the wells through the channels.

Additional features and advantages of the microplate apparatus and fluidic device described herein will be set forth in the detailed description which follows, and in part will be readily apparent to those skilled in the art from that description or recognized by practicing the embodiments described herein, including the detailed description which follows, the claims, as well as the appended drawings.

It is to be understood that both the foregoing general description and the following detailed description describe various embodiments and are intended to provide an overview or framework for understanding the nature and character of the claimed subject matter. The accompanying drawings are included to provide a further understanding of the various embodiments, and are incorporated into and constitute a part of this specification. The drawings illustrate the various embodiments described herein, and together with the description serve to explain the principles and operations of the claimed subject matter.

BRIEF DESCRIPTION OF THE DRAWINGS

FIG. 19 depicts a perspective view of a fluidic apparatus in fluid communication with the microplate and plate lid assembly of FIG. 16 according to one or more embodiments shown and described herein.

DETAILED DESCRIPTION

Figure 1:
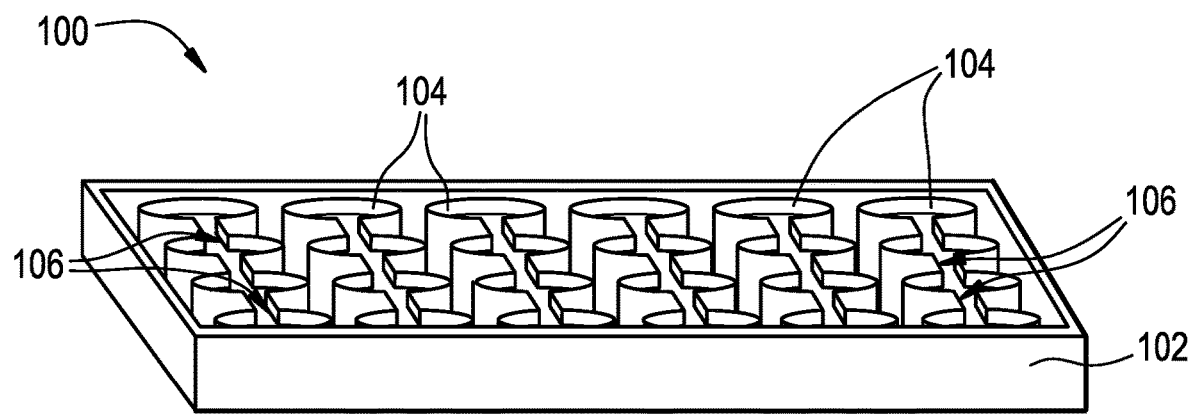
FIG. 1 depicts a perspective view of a microplate having multiple wells and multiple channels therein according to one or more embodiments shown and described herein.

Reference will now be made in detail to various embodiments of cell culture vessels with various stabilizer devices located therein, examples of which are illustrated in the accompanying drawings. Whenever possible, the same reference numerals will be used throughout the drawings to refer to the same or like parts. Directional terms as used herein—for example up, down, right, left, front, back, top, bottom, distal, and proximal—are made only with reference to the figures as drawn and are not intended to imply absolute orientation.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

Unless otherwise expressly stated, it is in no way intended that any method set forth herein be construed as requiring that its steps be performed in a specific order, nor that with any apparatus specific orientations be required. Accordingly, where a method claim does not actually recite an order to be followed by its steps, or that any apparatus claim does not actually recite an order or orientation to individual components, or it is not otherwise specifically stated in the claims or description that the steps are to be limited to a specific order, or that a specific order or orientation to components of an apparatus is not recited, it is in no way intended that an order or orientation be inferred, in any respect. This holds for any possible non-express basis for interpretation, including: matters of logic with respect to arrangement of steps, operational flow, order of components, or orientation of components; plain meaning derived from grammatical organization or punctuation, and; the number or type of embodiments described in the specification.

As used herein, the singular forms "a," "an" and "the" include plural referents unless the context clearly dictates otherwise. Thus, for example, reference to "a" component includes aspects having two or more such components, unless the context clearly indicates otherwise.

Referring now to FIG. 1, one embodiment of a microplate 100 comprises a body 102 including a plurality of wells 104 and a plurality of fluid flow channels 106 formed therein. In particular, each fluid flow channel 106 of the plurality of fluid flow channels 106 is positioned between two immediately adjacent wells 104 such that the plurality of wells 104 are interconnected with each other via the plurality of fluid flow channels 106. With each well 104 separated from an adjacent well 104 by fluid flow channel 106, fluid flow channel 106 effectively forms a gap between adjacent wells 104 on microplate 100. As will be described in greater detail below, the plurality of wells 104 are in fluid communication with one another via the plurality of fluid flow channels 106 that interconnect the plurality of wells 104 together. As will also be described further below, the plurality of fluid flow channels 106 are sized and shaped to facilitate fluid flow movement from one well 104 to an adjacent well 104 to promote the maturation and differentiation of the organoids grown within the plurality of wells 104.

In the present example, body 102 is formed of a plastic material such that wells 104 and fluid flow channels 106 are similarly molded from the plastic material; however, it should be understood that body 102, wells 104, and fluid flow channels 106 may be formed of various other suitable materials for culturing cells.

Figure 2:
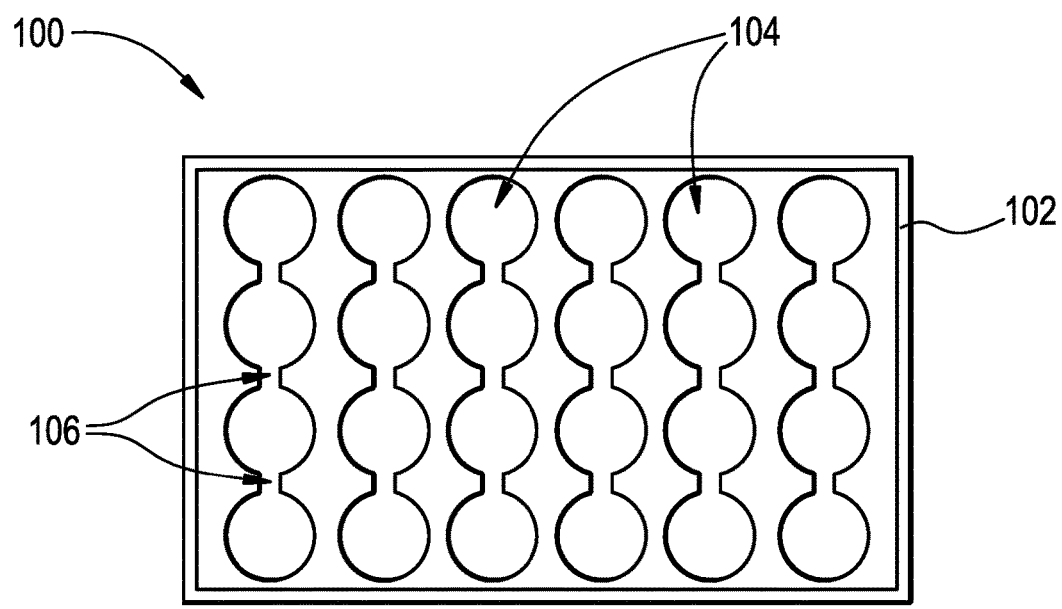
FIG. 2 depicts a top plan view of the microplate of FIG. 1 with the multiple channels extending along a column of multiple wells thereby interconnecting the column of multiple wells.
Figure 3:
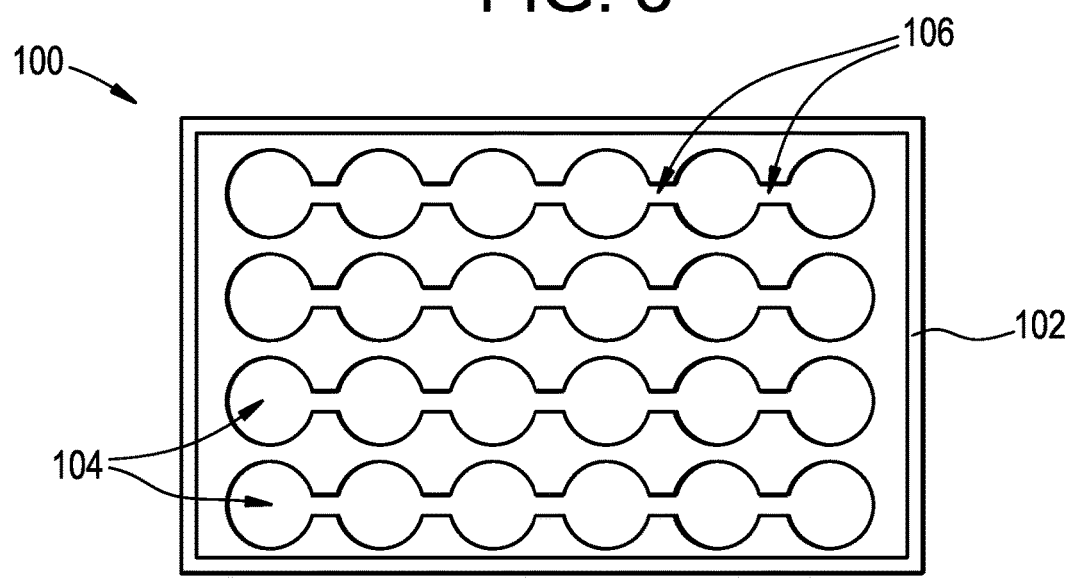
FIG. 3 depicts a top plan view of another embodiment of a microplate with the multiple channels along a row of multiple wells thereby interconnecting the row of multiple wells.

As best seen in FIG. 2, the plurality of fluid flow channels 106 extend laterally along the body 102 such that fluid flow channels 106 interconnect a column of wells 104 together. In this instance, microplate 100 includes various columns of wells 104 that are in fluid communication with one another via fluid flow channels 106 positioned therebetween. Alternatively, fluid flow channels 106 may be positioned within body 102 in various other orientations relative to wells 104 such that fluid flow channels 106 are configured to interconnect varying arrangements of wells 104 other than that shown in the present example. For example, as seen in FIG. 3, fluid flow channels 106 extend longitudinally along body 102 such that the plurality of fluid flow channels 106 interconnect a row of wells 104. In this instance, microplate 100 includes various rows of wells 104 that are in fluid communication with one another via fluid flow channels 106 positioned therebetween. Although not shown, it should be understood that other various arrangements of fluid flow channels 106 and wells 104 may be included in microplate 100.

Figure 4:
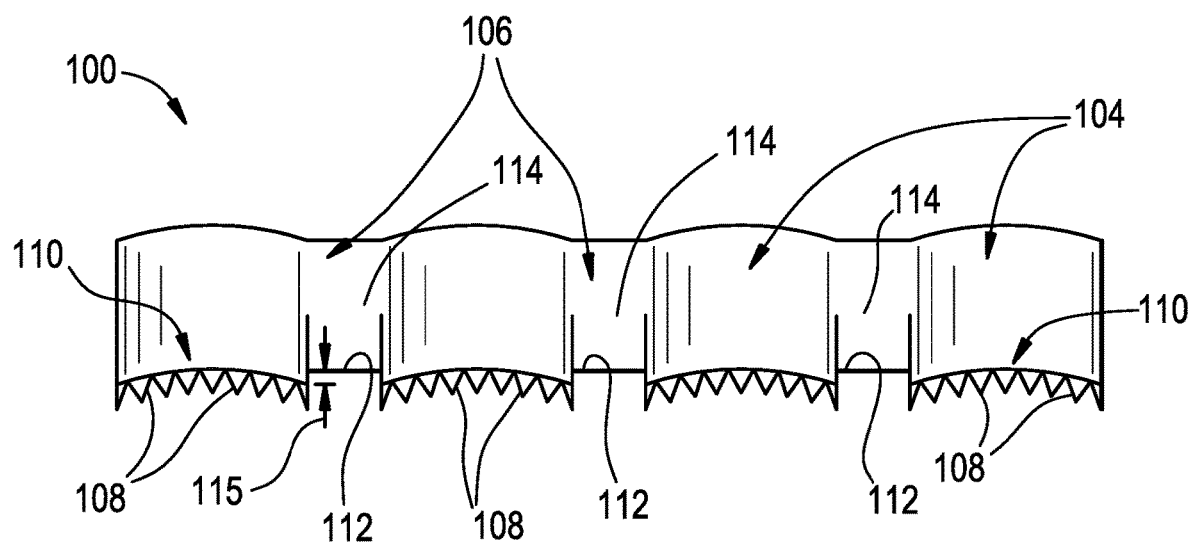
FIG. 4 depicts a side elevational view of the multiple wells and the multiple channels, the multiple wells including a microcavity substrate along a bottom wall of the well according to one or more embodiments shown and described herein.

FIG. 4 shows a row of wells 104 interconnected by a series of fluid flow channels 106. In the present example, the plurality of wells 104 comprise a plurality of microcavities 108 along a well floor 110 of each well 104. Microcavities (108) are micronized cavities formed along a planar surface, in this instance along a well floor 110 of wells 104, that each define a defined space respective of one another. Microcavities 108 are sized and shaped to receive a plurality of cells in each microcavity 108 for culturing. In the present example, well floor 110 of wells 104 comprise a cell culture substrate that is configured to enable formation of three-dimensional 3D) cell aggregates (i.e. spheroids). Accordingly, the plurality of microcavities 108 positioned along well floor 110 of wells 104 similarly comprise the cell culture substrate operable to facilitate the growth and development of spheroids from the cells (e.g. stem cells) received therein. In some instances, the cell culture substrate of microcavities 108 and well floor 110 may comprise a gas permeable material to further promote the formation of 3D cell aggregates within wells 104. It should be understood that microcavities 108 and well floor 110 may comprise other suitable materials for the growth and development of spheroids.

The plurality of fluid flow channels 106 of microplate 100 have a channel floor 112 that is elevated relative to well floor 110 of wells 104 to provide a gap 115 between fluid flow channels 106 and well floor 110. The plurality of fluid flow channels 106 further include a pair of sidewalls 114 extending upwardly relative to channel floor 112 thereby forming a volume within the fluid flow channels 106. Accordingly, gaps 115 are configured to partially store and/or maintain the plurality of cells initially received within the microcavities 108 within wells 104 despite the proximal connection of fluid flow channels 106. Sidewalls 114 are further configured to partially store and/or maintain any liquid medium or cells, transferred from the plurality of wells 104 into fluid flow channels 106, between sidewalls 114. In some instances, fluid flow channels 106 may similarly be configured to receive a plurality of cells therein for culturing and developing organoids. It should be understood that the plurality of fluid flow channels 106 may comprise a cell culture substrate along channel floor 112, similar to well floor 110 of wells 104, such that channel floor 112 of fluid flow channels 106 are configured to enable formation of 3D cell aggregates in conjunction with the plurality of wells 104.

Referring back to FIG. 3, fluid flow channels 106 are sized to have a width that is less than a width of wells 104 such that fluid flow channels 106 are dimensioned to include a narrower profile than wells 104. As merely an illustrative example, fluid flow channels 106 may include a width that is approximately 50% of the width of wells 104. As will be described in greater detail below, the width of fluid flow channels 106 serves to facilitate the transfer of matter through fluid flow channels 106 to further facilitate the development of the spheroids grown within the plurality of wells 104 that fluid flow channels 106 are connected to, respectively. The matter transferred by fluid flow channels 106 may be a liquid culture medium, fluids (e.g., including water), soluble factors, cells, or other various matter conducive for the growth of cultured cells. The relative size of fluid flow channels 106 to wells 104 further enables microplate 100 to be used with various suitable equipment for culturing cells within microplate 100, such as fluidic devices for perfusing the 3D cell cultures.

Figure 5:
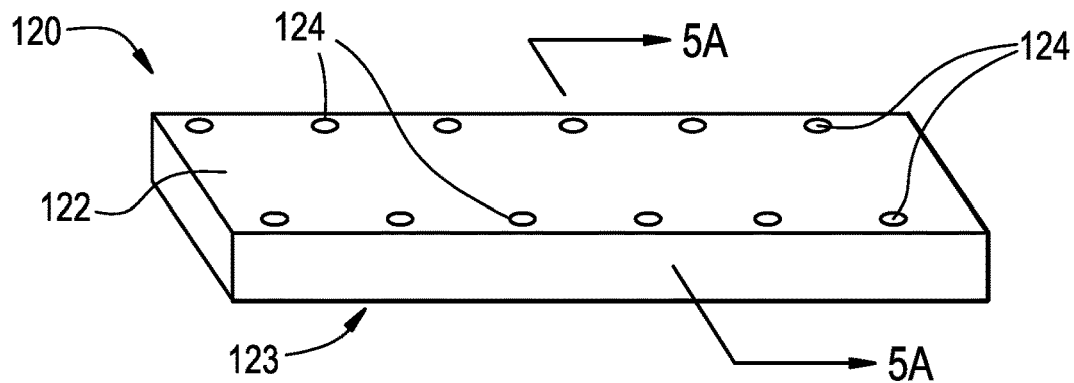
FIG. 5 depicts a perspective view of a plate lid having multiple ports extending along an external surface according to one or more embodiments shown and described herein.

FIG. 5 shows a plate lid 120 that is sized and shaped to engage microplate 100. Plate lid 120 includes an external surface 122 along a top side of plate lid 120. Plate lid 120 further includes a plurality of ports 124 along external surface 122 that extend through plate lid 120 from external surface 122 to an opposite surface 123. In this instance, the plurality of ports 124 are configured to provide access to the internal surface of plate lid 120 from external surface 122. As will be described in greater detail below, the plurality of ports 124 are sized and shaped to receive a tube therein for establishing fluid communication between the internal surface of plate lid 120 and a fluidic apparatus 130, for example, shown in FIG. 7. In the present example, plate lid 120 is formed of a clear plastic material such that opposite surface 123 of plate lid 120, wells 104 and fluid flow channels 106 may be visibly seen from external surface 122. It should be understood that in other versions, plate lid 120 may be formed of other suitable materials.

Figure 5A:
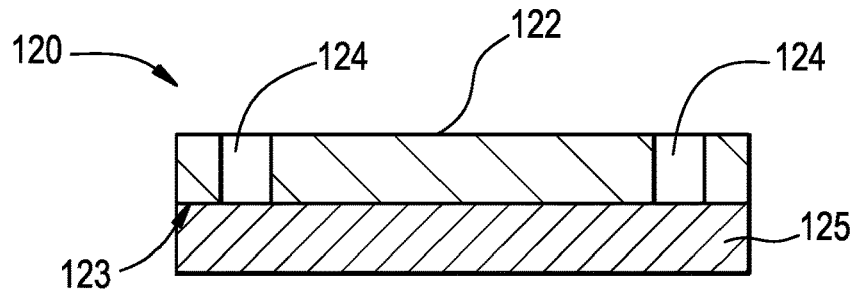
FIG. 5A depicts a cross sectional view of the plate lid of FIG. 5 and the microplate of FIG. 1 with an elastomer lining positioned therebetween according to one or more embodiments shown and described herein, the cross section taken along line A-A of FIG. 5.

In some instances, the internal surface of plate lid 120 may include an elastomer lining 125 thereon that is sized and shaped to cover the plurality of ports 124 at the opposite surface 123, as seen in FIG. 5A. In this instance, the elastomer lining 125 is configured to seal plate lid 120 to microplate 100 when plate lid 120 is assembled onto microplate 100 thereby securely fastening plate lid 120 to microplate 100. As merely an illustrative example, the elastomer lining 125 may be a silicone adhesive or other various sealant polymers. Additionally, elastomer lining 125 may be transparent or translucent to allow for viewing of microplate 100 positioned beneath plate lid 120. The elastomer lining 125 can also serve as a protective liner that separates the plurality of wells 104 and the plurality of fluid flow channels 106 from contacting the internal surface of plate lid 120. In this instance, the elastomer lining 125 seals wells 104 and fluid flow channels 106 to minimize risk for contaminating the contents of wells 104 and fluid flow channels 106.

Additionally or alternatively, the elastomer lining 125 may be further configured to form a septum between microplate 100 and plate lid 120, in particular the plurality of ports 124. In this instance, despite microplate 100 being assembled onto plate lid 120, the plurality of ports 124 may not be in communication with the plurality of wells 100 and/or fluid flow channels 106 of microplate 100 due to the presence of the elastomer lining 125 along the opposite surface 123 of plate lid 120. Accordingly, to establish access to the plurality of wells 104 and fluid flow channels 106 after plate lid 120 is assembled onto microplate 100, the septum created by the elastomer lining 125 may be pierced by a puncturing device. By way of example only, a cannula, needle, or other suitable puncturing device may be inserted into the plurality of ports 124 along external surface 122 to pierce the elastomer lining 125.

Figure 6:
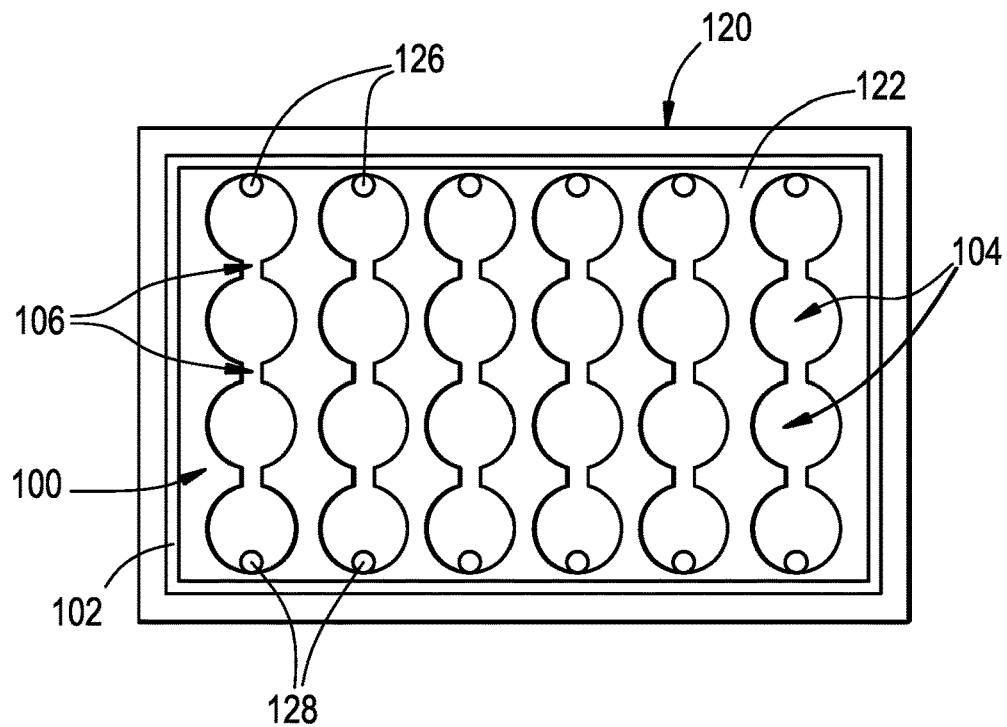
FIG. 6 depicts a top view of the plate lid assembled onto the microplate, with the multiple wells aligned over the multiple wells according to one or more embodiments shown and described herein.

FIG. 6 shows plate lid 120 assembled onto microplate 100 such that microplate 100 is received along the internal surface of plate lid 120. In this instance, with microplate 100 positioned within plate lid 120, the plurality of wells 104 and fluid flow channels 106 face upward into plate lid 120 and toward the internal surface of plate lid 120. The plurality of ports 124 are formed along external surface 122 of plate lid 120 to align with the positions of wells 104 of microplate 100 when plate lid 120 is assembled onto microplate 100. In other words, plate lid 120 is configured to correspond with the particular microplate 100 that plate lid 120 is intended to be assembled onto such that the plurality of ports 124 are positioned accordingly to align with the location of wells 104 in microplate 100. In the present example, microplate 100 includes the plurality of fluid flow channels 106 extending vertically across body 102, thereby connecting a column of wells 104. Accordingly, the plurality of ports 124 of plate lid 120 are positioned along a longitudinal length of external surface 122 to correspond with the positions of wells 104 such that each column of interconnected wells 104 is in communication with at least two ports 124 of plate lid 120. As will be described in greater detail below, one port 124 of the two ports 124 in communication with each column of interconnected wells 104 serves as an "incoming" access point into the column of wells 104 (hereinafter referred to as incoming port 126) and the other port 124 of the two ports 124 coupled to the column of wells 104 provides an "outgoing" access point (hereinafter referred to as outgoing port 128).

It should be understood that in other instances where microplate 100 includes a row of wells 104 interconnected with one another by the plurality of fluid flow channels 106, as previously described above and seen in FIG. 3, the plurality of ports 124 of plate lid 120 would be positioned along a width of external surface 122 to thereby correspond with the positions of wells 104 such that each row of interconnected wells 104 are in communication with two ports 124 of plate lid 120. Still other arrangements and positions of the plurality of ports 124 of plate lid 120 will be apparent to those of ordinary skill in the art in view of the arrangement of the plurality of wells 104 and the plurality of fluid flow channels 106 of microplate 100.

In use, the plurality of microcavities 108 of wells 104 are seeded with cells and plate lid 120 is thereafter assembled onto microplate 100 to enclose the cells therein. In this instance, the assembly of microplate 100 and plate lid 120 may be positioned within an incubator that comprises a rocker table. The incubator is activated thereby providing movement of rocker table with microplate 100 located thereon which provides for the formation of spheroids and/or organoids within the plurality of wells 104 and/or fluid flow channels 106 therein. Subsequently, the assembly of microplate 100 and plate lid 120 is removed from the incubator and plate lid 120 is disassembled from microplate 100. In this instance, the plurality of wells 104 and fluid flow channels 106 may be flooded with a liquid culture medium such that the spheroids and/or organoids developed therein are submerged with the liquid culture medium.

Figure 7:
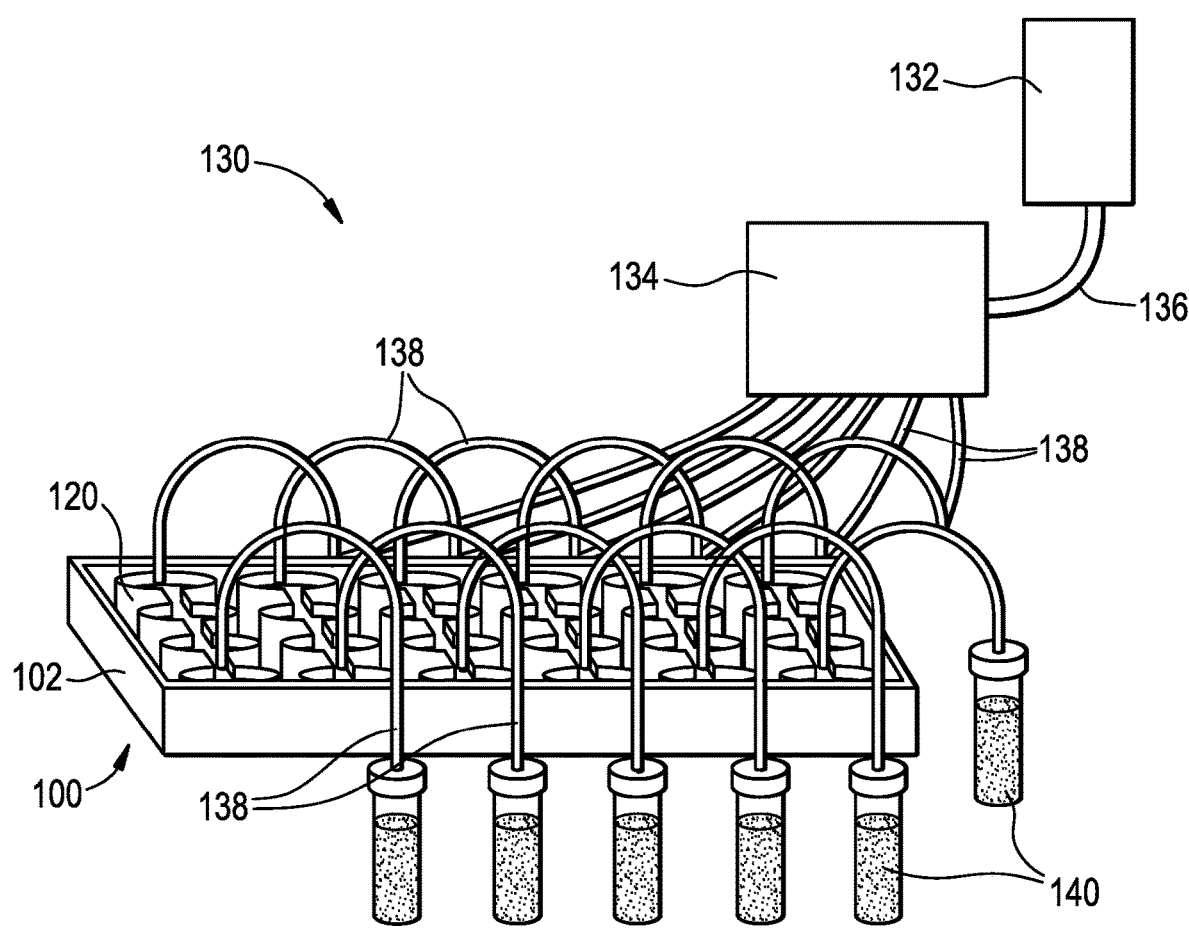
FIG. 7 depicts a perspective view of a fluidic apparatus in fluid communication with the microplate and plate lid assembly according to one or more embodiments shown and described herein.

Plate lid 120 is thereafter reassembled onto microplate 100 and the assembly of plate lid 120 and microplate 100 are connected to a fluidic apparatus 130, as seen in FIG. 7. In this instance, access to the plurality of wells 104 and fluid flow channels 106 is solely provided through the plurality of ports 124 of plate lid 120. With the assembly of microplate 100 and plate lid 120 coupled to fluidic apparatus 130, fluidic apparatus 130 establishes fluid communication with the plurality of wells 104 and fluid flow channels 106 through the plurality of ports 124 of plate lid 120. Generally, fluidic apparatus 130 is configured to perfuse the plurality of wells 104 and fluid flow channels 106 with a liquid to thereby expose the spheroids and/or organoids included therein to a shear force.

Fluidic apparatus 130 comprises an external fluid source 132, a fluid distribution device 134, and an external fluid reservoir 140. External fluid source 132 is coupled to fluid distribution device 134 via a conduit 136 disposed therebetween thereby establishing fluid communication between external fluid source 132 and fluid distribution device 134. In the present example, fluid external source 132 is a pressurized media bag containing a fluid therein. Further, fluid distribution device 134 is a manifold that includes a flow control valve for each interconnected column of wells 104 included in microplate 100, respectively. Accordingly, each flow control valve of fluid distribution device 134 (i.e. the manifold) is coupled to incoming port 126 of the plurality of ports 124 that is aligned with the respective column of interconnected wells 104. The flow control valves are configured to selectively manage (i.e. controllably release) an amount and rate of fluid from external fluid source 132 to incoming ports 124. Fluid distribution device 134 is coupled to the assembly of plate lid 120 and microplate 100 via a series of tubes 138 extending between the flow control valves of fluid distribution device 134 and the plurality of incoming ports 126.

The fluid control valves of fluid distribution device 132 are actuated to initiate transfer of the fluid from external fluid source 132, through fluid distribution device 132, and toward incoming ports 126 of plate lid 120 via the series of tubes 138. Upon reaching incoming ports 126, the fluid enters a first well 104 of the interconnected column of wells 104. The cell culture substrate of well floor 110 is exposed to the fluid flow such that the cells and the liquid medium stored within microcavities 108 are perfused. The fluid is transferred through the other plurality of wells 104 that are interconnected with the first well 104 via the plurality of fluid flow channels 106 connecting the first well 104 with the remaining plurality of wells 104. As the fluid travels through the plurality of wells 104 via the plurality of fluid flow channels 106, the flow generates a shear force through the wells 104 and fluid flow channels 106. Accordingly, perfusing the plurality of wells 104 via the connectivity provided by the plurality of fluid flow channels 106 exposes the contents of wells 104 and fluid flow channels 106 (i.e. the cells and liquid medium received along the culture substrate of microcavities 108 and well floor 110) to a shear force/stress that effectively differentiates the cell culture substrate of wells 104 and aids in cell differentiation and maturation of organoids within wells 104 and/or fluid flow channels 106.

In other words, by inducing a constant fluid flow along the spheroids formed within the plurality of wells 104, due to the connectivity of wells 104 by the plurality of fluid flow channels 106, the 3D cell aggregates grown along well floors 110 mature with differentiated functions. If different organoids are grown in each well 104 of the plurality of wells 104, then perfusing the column of interconnected wells 104 with fluid will circulate soluble factors that further encourage differentiated function, which aids in forming organoids that closely simulate a functional representation of human organs. The shear force/stress induced within microplate 100 is partly attributable to the flow of fluid transferred from fluid distribution device 134 and partly attributable to the size and shape of fluid flow channels 106. In particular, as described in detail above, fluid flow channels 106 are sized to provide an enhanced conduit for the fluid to travel through such that the plurality of fluid flow channels 106 are configured to create ample fluid movement within each well 104 for providing cell differentiation and maturation of the organoids grown therein.

As the fluid flows through the plurality of wells 104, the gap 115 below each fluid flow channel 106 partially retains the spheroids and/or organoids developed along microcavities 108 of well floor 110 within the respective well 104. The pair of sidewalls 114 are sized and shaped to simultaneously permit the fluid to flow through the plurality of channels 106 at a sufficient rate to thereby facilitate formation of the necessary shear stress along the 3D cell aggregates of each well 104 to mature the organoids positioned therein. Accordingly, the size and shape of the plurality of fluid flow channels 106 serve multiple purposes as the fluid is perfused through microplate 100. Once the fluid reaches the last well 104 in the linear column of wells 104, the fluid is transferred out of microplate 100 via the respective outgoing port 128 that is aligned with the last well 104 of each interconnected column of wells 104. In this instance, each outgoing port 128 is coupled to a tube 138 that is coupled to plate lid 124 at external surface 122 at one end and to external fluid reservoir 140 at an opposite end. External fluid reservoir 140 collects the circulated fluid from microplate 100 for storage and subsequent discarding.

Although not shown, it should be understood that in some versions fluidic apparatus 130 may not include external fluid reservoir 140, rather, the circulated fluid is rerouted to thereby flow through the plurality of wells 104 and fluid flow channels 106 repeatedly until the perfusion cycle ceases. In this instance, outgoing ports 128 may be coupled to incoming ports 126 via a series of tubes 138 such that the fluid is recirculated from the last well 104 and to the first well 104 such that the fluid is transferred through the same linear column of wells 104 and fluid flow channels 106 for a predetermined number of cycles.

Additionally or alternatively, in some instances microplate 100 may be positioned within a heating device that is configured to raise the temperature of microplate 100. In this instance, with the assembly of microplate 100 and plate lid 120 received within the heating device, the internal temperature of the contents stored within the plurality of wells 104 and fluid flow channels 106 (i.e. 3D cell aggregates, liquid medium, fluid, etc.) is controllably raised to a predetermined temperature to thereby provide various advantages, including but not limited to maintaining cell viability and cellular metabolism. Accordingly, as the fluid is transferred through the linear columns of wells 104 and fluid flow channels 106 to generate the necessary shear stress for promoting development of the organoids stored therein, the heating device simultaneously heats the cells to maintain their viability.

In other versions, fluid distribution device 134 of fluidic apparatus 130 comprises a pump coupled to the assembly of microplate 100 and plate lid 120 via tubes 138. Although not shown, it should be understood that the method of use of fluidic apparatus 130 is substantially similar as explained in detail above except for the differences explicitly noted herein. In this instance, fluid distribution device 134 (i.e. the pump) is configured to output the fluid, rather than merely release the fluid as described above with the manipulation of control valves of a manifold, at a predetermined flowrate such that the necessary shear stress is generated by setting a corresponding mechanical displacement that thereby produces a sufficient velocity for fluid. As merely an illustrative example, fluid distribution device 134 may be a peristaltic pump, however, it should be understood that other suitable pumps may be used as part of fluidic apparatus 130.

Figure 8:
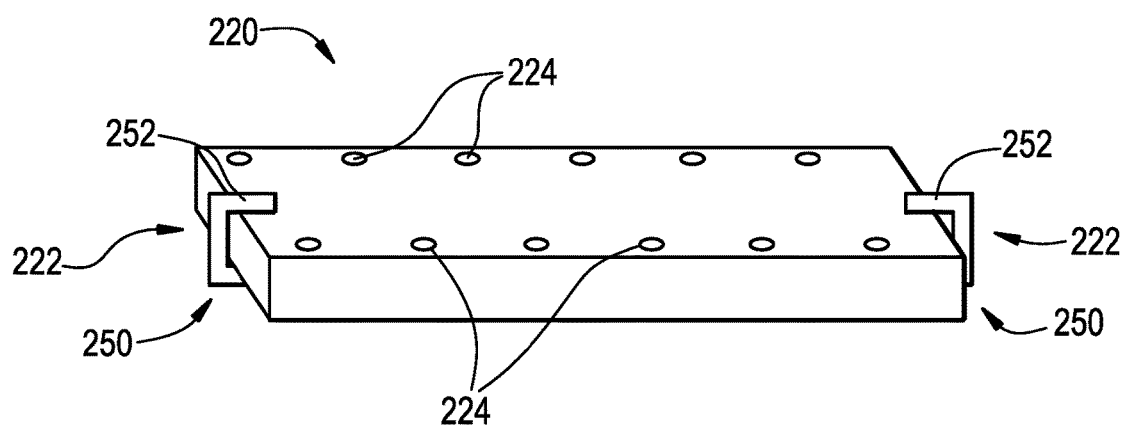
FIG. 8 depicts a perspective view of the plate lid and a fastening mechanism that securely engages the microplate to the plate lid according to one or more embodiments shown and described herein.

FIG. 8 shows another embodiment of a plate lid 220 that comprises a fastening mechanism 250. Except as otherwise described below, plate lid 220 is configured and operable just like plate lid 120 described above. Fastening mechanism 250 is configured to securely engage plate lid 220 to microplate 100 when microplate 100 is received within plate lid 220. In the present example, fastening mechanism 250 comprises a pair of clamp arms 252 secured to plate lid 220 along outer ends 222 of plate lid 220. In particular, clamp arms 252 are movable relative to plate lid 220 to thereby tightly grasp microplate 100 and thereby seal microplate 100 to the internal surface of plate lid 220. Although not shown, it should be understood that fastening mechanism 250 may comprise various other forms of fastening devices. As merely an illustrative example, fastening mechanism 250 may comprise snap features that are configured to engage associated features along microplate 100. Alternatively, by way of further example only, fastening mechanism 250 may comprise an adhesive that is operable to securely seal plate lid 220 to microplate 100.

Figure 9:
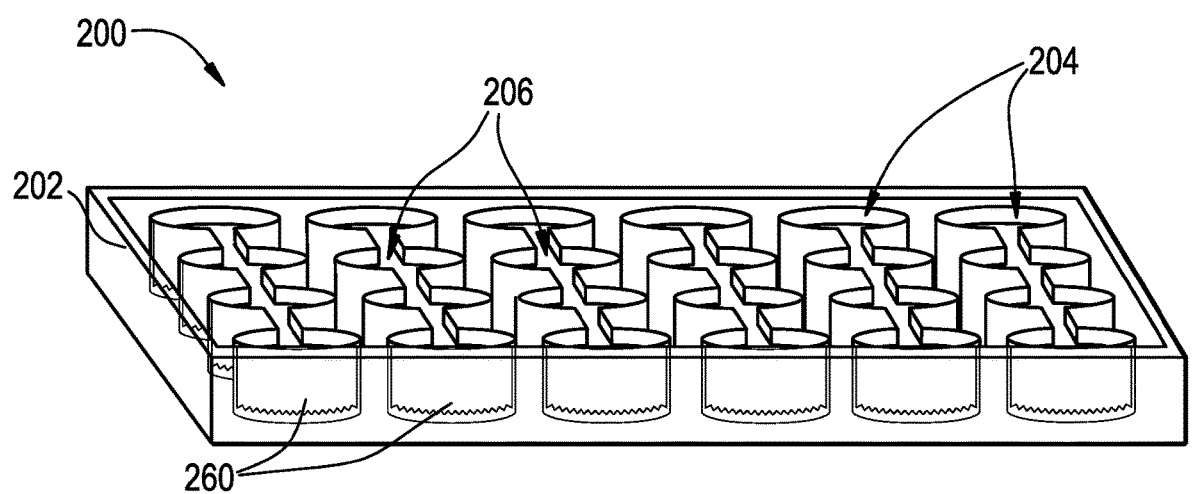
FIG. 9 depicts a partial perspective view of the microplate including an insert received within the multiple wells according to one or more embodiments shown and described herein.
Figure 10:
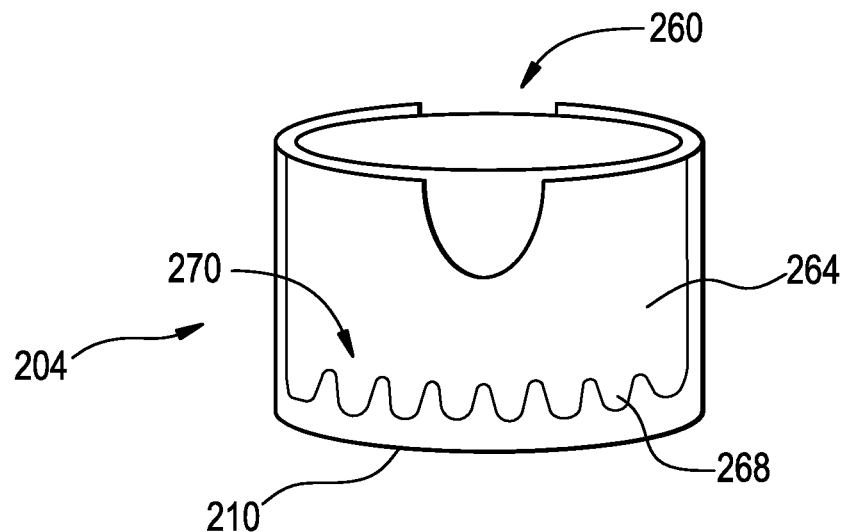
FIG. 10 depicts a partial perspective view of the well of the microplate with the insert received therein, the insert having a microcavity geometry according to one or more embodiments shown and described herein.
Figure 11:
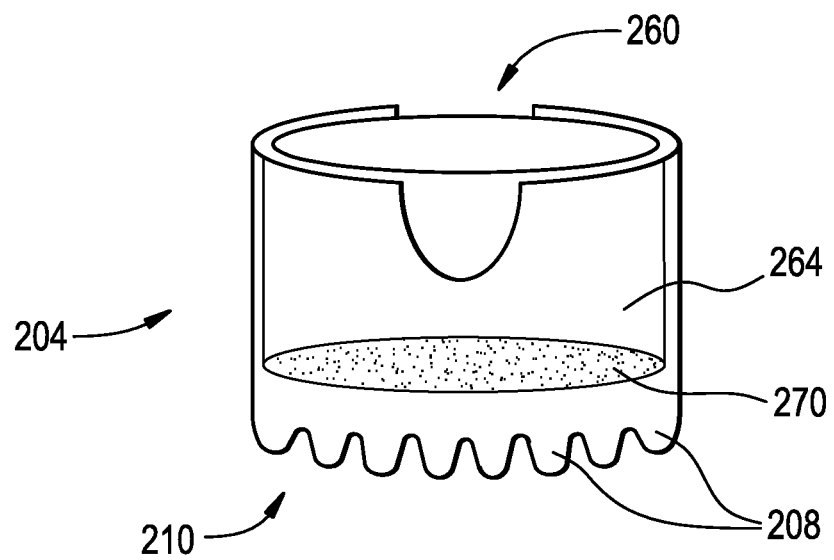
FIG. 11 depicts a partial perspective view of the well of the microplate with the insert received therein, the well having a microcavity-geometry according to one or more embodiments shown and described herein.

FIG. 9, FIG. 10, and FIG. 11 show another embodiment of a microplate 200 including an insert 260 received therein. Except as otherwise described below, microplate 200 is configured and operable similar to microplate 100 described above. Therefore, like reference numerals are used to identify like components of microplate 200. Insert 260 includes a plurality of well inserts 264 that are sized and shaped to fit within the plurality of wells 204 of microplate 200. In the present example, insert 260 is formed of a porous material such that well inserts 264 are configured to be in fluid communication with wells 204 when well inserts 264 are received within wells 204. As will be described in greater detail below, by being formed of a porous material, insert 260 is operable to permit co-culturing of the cells positioned within microplate 200 when well inserts 264 of insert 260 are received over well floor 210 of each well 204.

Although not shown, it should be understood that insert 260 may further comprise a plurality of channel inserts that are sized and shaped to fit within the plurality of fluid flow channels 206 of microplate 200. Further, it should be understood that the plurality of well inserts 264 and/or the plurality of channel inserts of insert 260 may be unitarily secured with one another. In this instance, each well 204 and/or fluid flow channel 206 of microplate 200 is covered by the porous membrane of insert 260 when insert 260 is positioned therein. Alternatively, in other versions the plurality of well inserts 264 and/or the plurality of channel inserts of insert 260 may be individually separable from one another such that a user may selectively insert a well insert 264 and/or channel insert into respective wells 204 and/or fluid flow channels 206 as desired. In this instance, not every well 204 or fluid flow channel 206 of microplate 200 is covered by insert 260.

In some versions, unlike the plurality of wells 104 of microplate 100 described above, the plurality of wells 204 of microplate 200 has a planar surface along well floor 210 such that well floor 210 does not include a plurality of microcavities formed therein, as seen in FIG. 10. Rather, well inserts 264 of insert 260 comprise a plurality of microcavities 268 along well insert floor 270 of well inserts 264. In this instance, well floor 210 is still configured to receive cells thereon despite the absence of microcavities therein. Further, well insert floor 270 is configured to receive cells within microcavities 268 and thereby form spheroids/organoids therein. Accordingly, the cells deposited along well floor 210 of wells 204 are in communication with the spheroids/organoids formed in microcavities 268 of well inserts 264 during perfusion since insert 260 is formed of a porous membrane.

Alternatively, in other versions as seen in FIG. 11, the plurality of wells 204 of microplate 200 include a plurality of microcavities 208 along well floor 210, similar to wells 104 of microplate 100. In this instance, well insert floor 270 of well inserts 264 include a planar surface such that well insert floor 270 does not have microcavities formed therein. Accordingly, the spheroids/organoids formed within microcavities 208 of well floor 210 remain in communication with any cells and/or fluid along well insert floor 270 of well inserts 264 due to insert 260 being comprised of a porous material. Although not shown, it should be understood that both well floor 210 and well insert floor 270 may comprise other combinations of geometric surfaces. As merely an illustrative example, both well floor 210 of microplate 200 and well insert floor 270 of insert 260 may include microcavities that are similarly sized and shaped to thereby permit the microcavities of well floor 210 to receive the microcavities of well insert floor 270 therein.

In use, the plurality of wells 204 are seeded with cells as described above irrespective of whether well floors 210 include microcavities 208. With wells 204 including cells therein, insert 260 is positioned within microplate 200 such that the plurality of well inserts 264 and/or channel inserts are received within wells 204 and/or fluid flow channels 206, respectively. In this instance, the seeded cells are securely contained between well floors 210 and well insert floors 270 of the plurality of well inserts 264. With insert 260 securely received by microplate 200, the plurality of well inserts 264 are seeded with cells prior to assembling plate lid 120 onto microplate 200 with insert 260 enclosed therein.

In this instance, as similarly described above, the assembly of microplate 200 and plate lid 120 are positioned within an incubator to thereby provide movement of microplate 200 for the formation of spheroids and/or organoids within the plurality of wells 104 and/or plurality of well inserts 264. Subsequently, the assembly of microplate 200 and plate lid 120 is removed from the incubator and plate lid 120 is disassembled from microplate 200 such that microplate 200 and insert 260 may be flooded with a liquid culture medium. In this instance, the spheroids and/or organoids developed within wells 204 and/or well inserts 264 are effectively submerged with the liquid culture medium.

Plate lid 120 is thereafter reassembled onto microplate 200 and the assembly of plate lid 120 and microplate 100 is connected to a fluidic device, similar to fluidic apparatus 130 described above and seen in FIG. 7. Accordingly, any fluid transferred through microplate 200 by fluidic apparatus 130 will perfuse the organoids developed along both the plurality of well inserts 264 of insert 260 and the plurality of wells 204 of microplate 200. In particular, since insert 260 is formed of a porous material, the shear stress produced by the transfer of fluid along insert 260 is still experienced by the cells disposed underneath insert 260 due to the porous nature of insert 260. In other words, despite the plurality of well inserts 264 and/or channel inserts covering the plurality of wells 204 and/or fluid flow channels 206, respectively, the cells deposited within wells 204 and channels 206 are still exposed to the shear force of the fluid perfused through microplate 200 by fluidic apparatus 130. Other steps and methods of culturing and perfusing microplate 200 and the organoids contained therein will be apparent to those of ordinary skill in the art in view of the teachings described above with respect to fluidic apparatus 130 and microplate 100.

Figure 12:
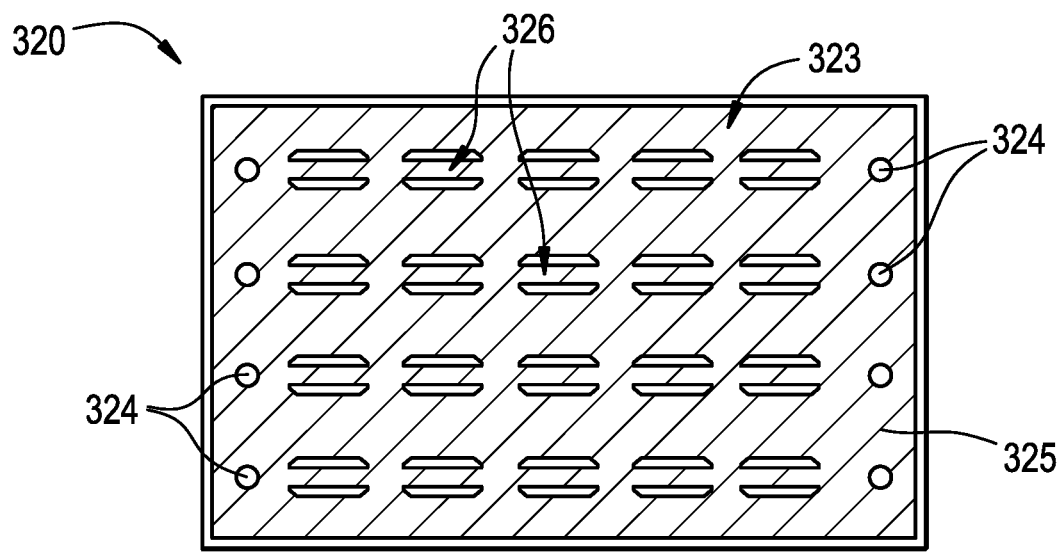
FIG. 12 depicts a top plan view of another embodiment of a plate lid having an internal elastomer lining and multiple fluid flow channels formed therein, the fluid flow channels extending laterally across the elastomer lining in linear rows.

FIG. 12 shows another embodiment of a plate lid 320 including an elastomer lining 325 formed along an internal surface 323 of plate lid 320. Except as otherwise described below, plate lid 320 is configured and operable similar to plate lid 120 described above. Therefore, like reference numerals are used to identify like components of plate lid 320. Plate lid 320 includes a plurality of ports 324 that extend between internal surface 323 and an opposite, external surface 322 of plate lid 320, similar to ports 124 described above. As will be described in greater detail below, elastomer lining 325 is sized and shaped to cover the plurality of ports 324 along internal surface 323. Plate lid 320 further includes a plurality of fluid flow channels 326 formed within elastomer lining 325. In other words, elastomer lining 325 comprises a plurality of linear cavities extending thereon at the plurality of fluid flow channels 326 such that elastomer lining has a depressed surface at the locations of fluid flow channels 326. As seen in FIG. 12, the plurality of fluid flow channels 326 extend laterally across internal surface 323 thereby forming four rows of fluid flow channels 326 on plate lid 320. It should be understood that other various quantities, arrangements, and orientations of fluid flow channels 326 may be included along elastomer lining 325 of plate lid 320, as will be described in greater detail below.

Figure 13:
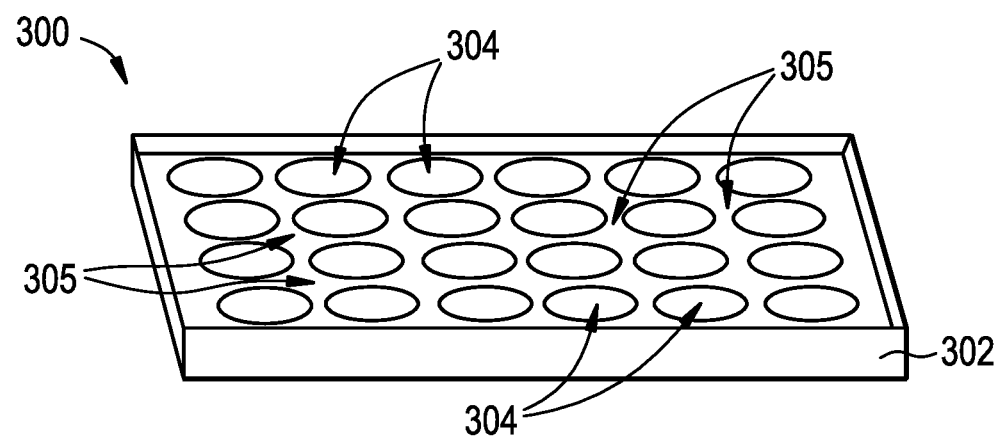
FIG. 13 depicts a perspective view of another embodiment of a microplate having multiple wells separately isolated from one another along a planar face.

FIG. 13 shows another embodiment of a microplate 300 including a plurality of wells 304 formed therein. It should be understood that microplate 300 is configured and operable just like microplate 100 described above, except for the differences explicitly noted herein. Unlike microplate 100, microplate 300 does not include a plurality of fluid flow channels formed thereon to interconnect the plurality of wells 304. Rather, the plurality of wells 304 are separated from one another by a flat plane surface 305 of microplate 300. Accordingly, the plurality of wells 304 of microplate 300 are individually isolated from one another by flat plane surfaces 305 such that the plurality of wells 304 are not in fluid communication with one another. Microplate 300 is configured to couple with plate lid 320 such that the plurality of ports 324 and the plurality of fluid flow channels 326 are operable to establish fluid communication with the plurality of wells 304 of microplate 300 in response to the engagement of plate lid 320 to microplate 300. Elastomer lining 325 is configured to seal plate lid 320 to microplate 300 when plate lid 320 is assembled onto microplate 300, thereby securely fastening plate lid 320 to microplate 300.

Figure 14:
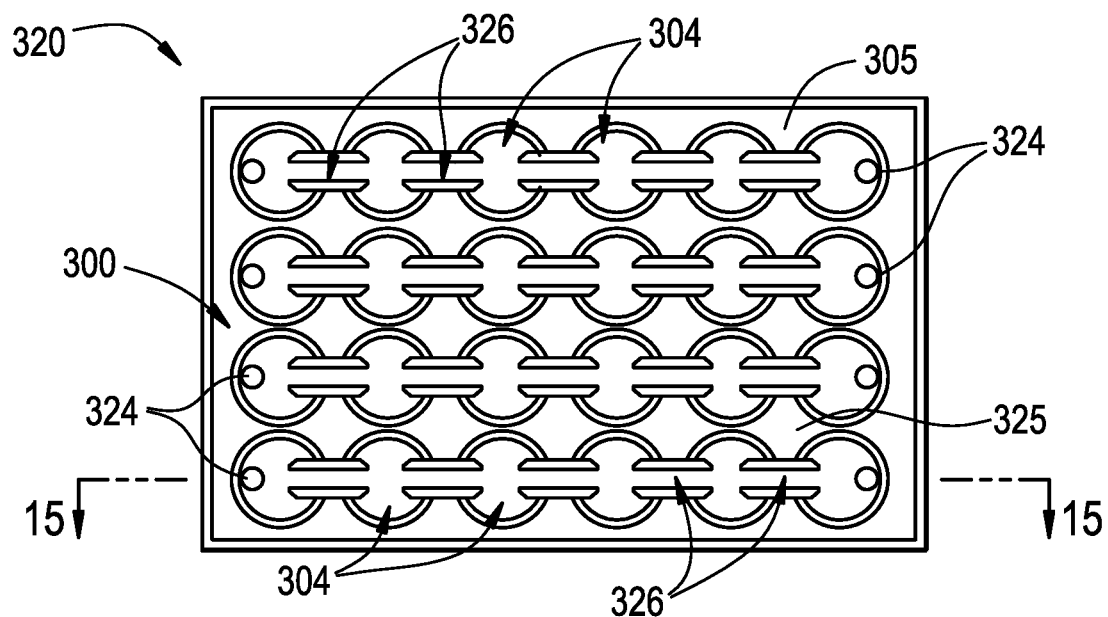
FIG. 14 depicts a top plan view of the plate lid of FIG. 12 assembled onto the microplate of FIG. 13, with the fluid flow channels of the plate lid interconnecting the multiple wells of the microplate.

As seen in FIG. 14, with plate lid 320 assembled atop microplate 300, each fluid flow channel 326 of the plurality of fluid flow channels 326 effectively extends between a pair of wells 304 of the plurality of wells 304 such that fluid flow channels 326 provide a pathway for fluid communication between the plurality of wells 304. With the plurality of fluid flow channels 326 extending laterally across internal surface 323 of plate lid 320, the plurality of fluid flow channels 326 are configured to provide fluid communication across a row of wells 304 on microplate 300. As will be described in greater detail below, different orientations of fluid flow channels 326 along internal surface 323 may provide other arrangements of communication amongst the plurality of wells 304 of microplate 300.

Figure 15:
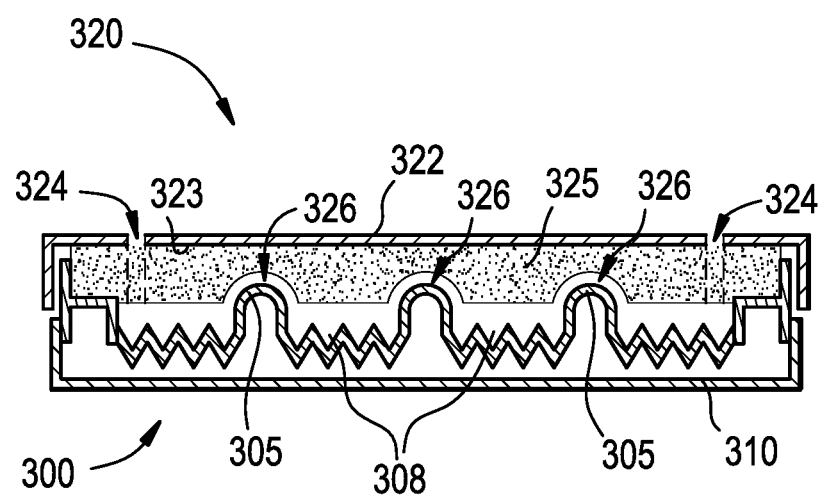
FIG. 15 depicts a cross-sectional view of the plate lid of FIG. 12 assembled onto the microplate of FIG. 13, the cross-section taken along line 15-15 of FIG. 14.

FIG. 15 shows the alignment of the plurality of fluid flow channels 326 with the plurality of wells 304 when plate lid 320 is securely coupled to microplate 300. The plurality of wells 304 include a plurality of microcavities 408 along well floors 410, similar to wells 104 of microplate 100 described above. Elastomer lining 325 provides a tight seal between plate lid 320 and microplate 300 and serves to ensure the contents of the plurality of wells 304 are maintained therein when plate lid 320 is assembled thereon. The plurality of fluid flow channels 326 of plate lid 320 are aligned between a pair of the plurality of wells 304 to thereby provide fluid communication between a row of wells 304. Elastomer lining 325 is recessed and/or depressed to form fluid flow channels 326 at flat plane surfaces 305 of microplate 300 between a pair of the plurality of wells 304 when plate lid 320 is assembled onto microplate 300. In other words, elastomer lining 325 does not contact microplate 300 at flat plane surface 305 extending between a pair of wells 304 of the plurality of wells 304, thereby not sealing a rim edge of the plurality of wells 304. Alternatively, as will be described in greater detail below, it should be understood that elastomer lining 325 may include other profiles for fluid flow channels 326 to thereby create a tight seal along the rim edges of wells 304 and the portion of microplate 300 extending between a pair of wells 304.

As briefly described above and as best seen in FIG. 15, elastomer lining 325 covers the plurality of ports 324 along internal surface 323 such that elastomer lining 325 must be punctured or pierced to access the plurality of wells 304. In other words, elastomer lining 325 may be further configured to form a septum between microplate 300 and plate lid 320, in particular the plurality of ports 324. In this instance, despite microplate 300 being assembled onto plate lid 320, the plurality of ports 324 may not be in communication with the plurality of wells 304 of microplate 300 due to the presence of the elastomer lining 325 along internal surface 323 of plate lid 320. Accordingly, to establish access to the plurality of wells 304 after plate lid 320 is assembled onto microplate 300, the septum created by elastomer lining 325 may be pierced by a puncturing device. By way of example only, a cannula, needle, or other suitable puncturing device may be inserted into the plurality of ports 324 along external surface 322 to pierce the elastomer lining 325.

As merely an illustrative example, elastomer lining 325 may be a silicone adhesive or other various sealant polymers. Additionally, elastomer lining 125 may be transparent or translucent to allow for viewing of microplate 300 positioned beneath plate lid 320. Elastomer lining 325 can also serve as a protective liner that separates the plurality of wells 304 from contacting internal surface 323 of plate lid 320. In this instance, elastomer lining 325 seals wells 304 to minimize risk for contaminating the contents of wells 304.

Figure 16:
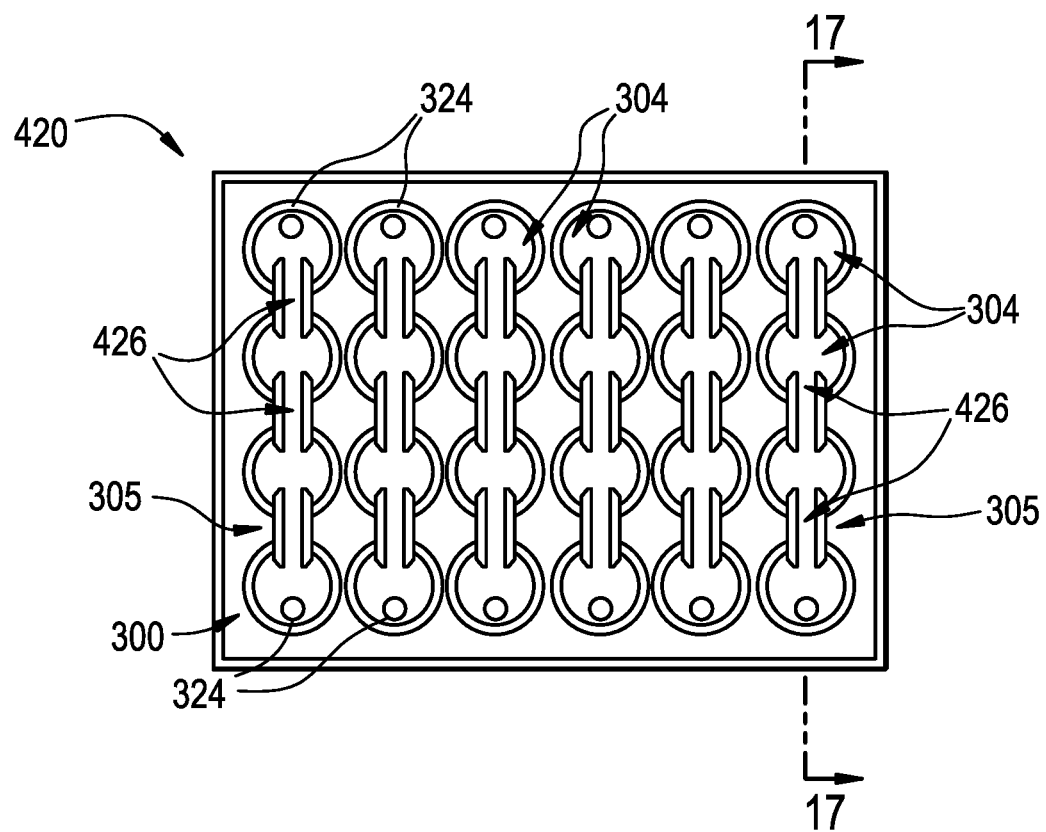
FIG. 16 depicts a top plan view of an alternative plate lid assembled onto the microplate of FIG. 13, the plate lid having an internal elastomer lining and multiple fluid flow channels formed therein, the fluid flow channels extending longitudinally across the elastomer lining in linear columns.
Figure 17:
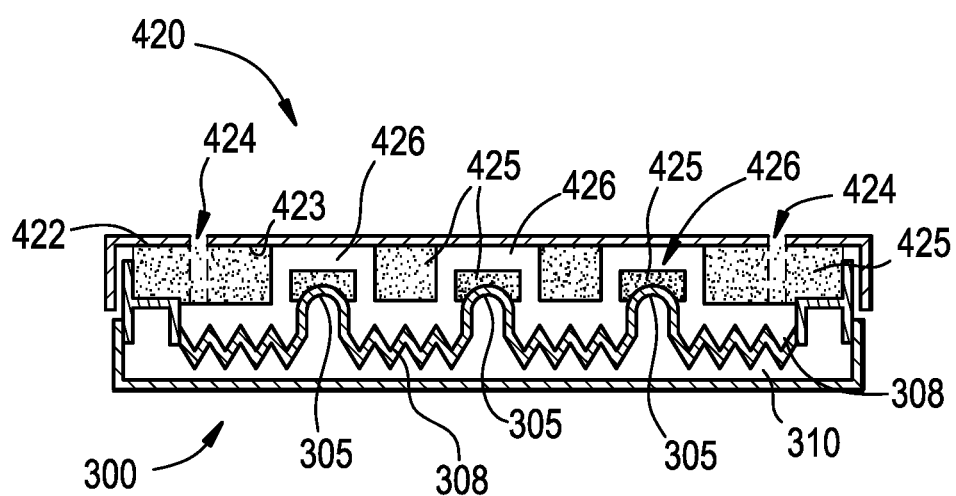
FIG. 17 depicts a cross-sectional view of the plate lid of FIG. 16 assembled onto the microplate of FIG. 13, the cross-section taken along line 17-17 of FIG. 16.

FIG. 16 shows another plate lid 420 that is substantially similar to plate lid 320 except that the plurality of fluid flow channels 426 are formed along an elastomer lining 425 to extend longitudinally relative to internal surface 423, rather than laterally as described above with respect to fluid flow channels 326 of plate lid 320. In other words, the plurality of fluid flow channels 426 of plate lid 420 extend vertically relative to elastomer lining 425 thereby providing fluid communication between the plurality of wells 304, when plate lid 420 is coupled to microplate 400, along a series of interconnected columns of wells 304 rather than a series of rows as provided by plate lid 320. Further, as seen in FIG. 17, elastomer lining 425 of plate lid 420 is configured to abut against flat plane surface 305 of microplate 300 extending between a plurality of wells 304 such that elastomer lining 425 provides a seal along the rim edges of the plurality of wells 304 when plate lid 420 is coupled to microplate 300. Accordingly, elastomer lining 425 provides a 360 degree seal along each well 304 of the plurality of wells 304. This may be provided by initially molding elastomer lining 425 to the flat plane of microplate 300 and thereafter sealing elastomer lining 425 to internal surface 423 of plate lid 420. The plurality of fluid flow channels 426 are offset from flat plane surface 305 of microplate 300 extending between the plurality of wells 304, thereby comprising a larger profile relative to the profile of fluid flow channels 326 of plate lid 320 described above. In this instance, elastomer lining 425 provides fluid communication between a column of plurality of wells 304 via fluid flow channels 326 extending therebetween while also maintaining a fluid seal between the each of the plurality of wells 304 of microplate 300.

With fluid flow channels 326, 426 formed on plate lid 320, 420, rather than on a microplate 300 as described above with respect to microplates 100, 200, respectively, various arrangements of fluid flow channels 326, 426 may be employed by simply changing the type of plate lid 320, 420 used in conjunction with microplate 300. This provides greater flexibility in selecting the method in which the cells are to be grown in microplate 300 due to the available combination of the culture conditions in which the plurality of wells 304 may be exposed to. For instance, different tissue models may initially be grown in different rows of microplate 300 by coupling plate lid 320 to microplate 300. Subsequently, plate lid 320 may be detached from microplate 300 and alternative plate lid 420, having different fluid flow channels 426 of varying configuration (e.g. extending longitudinally in a series of columns) than plate lid 320, may be coupled to microplate 300 to differentiate the media interaction between the different tissue models contained within adjacent wells 304 of microplate 300.

Figure 18:
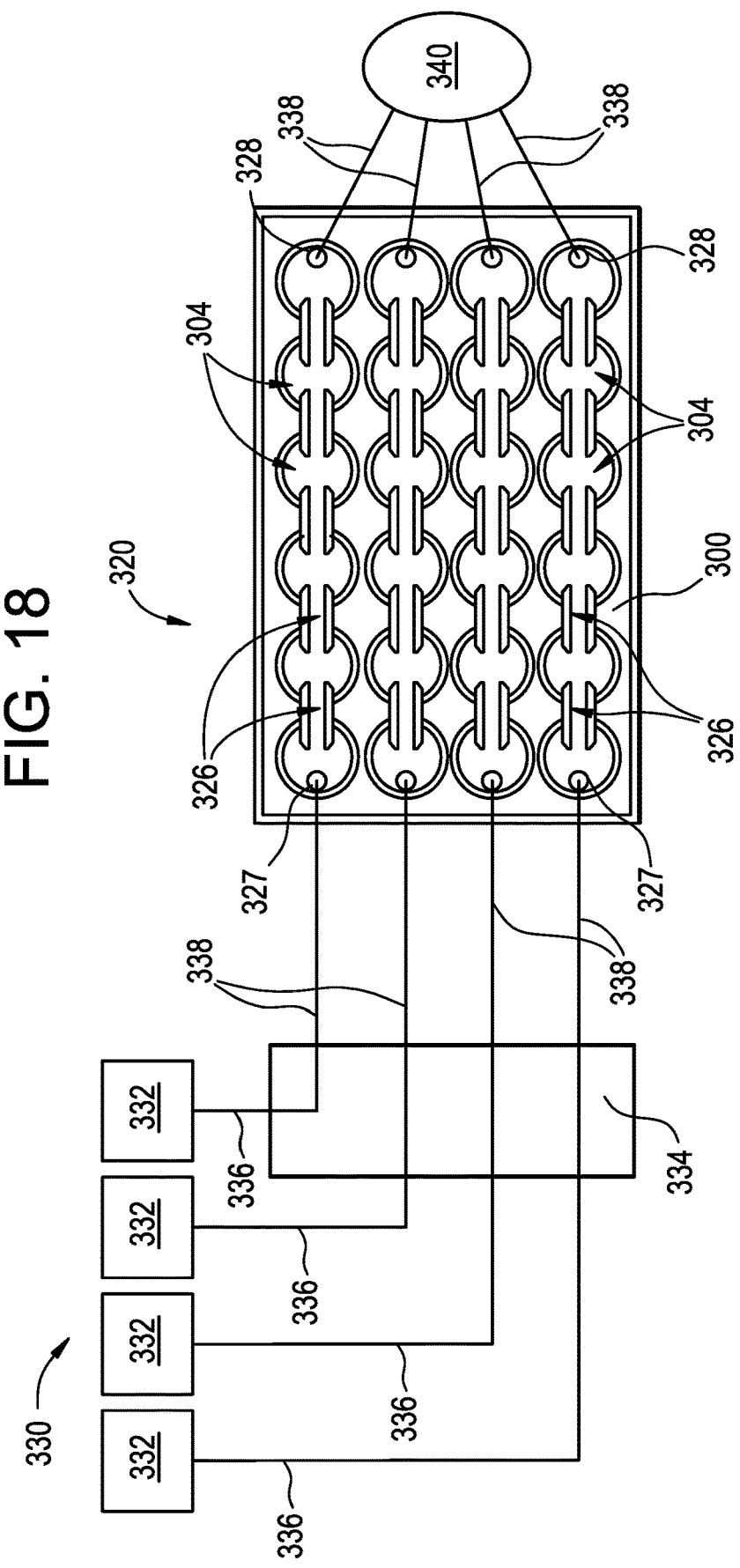
FIG. 18 depicts a perspective view of a fluidic apparatus in fluid communication with the microplate and plate lid assembly of FIG. 14 according to one or more embodiments shown and described herein.

It should be understood that plate lids 320, 420 and microplate 300 are operable with a fluidic device in a substantially similar manner as plate lid 120, 220 and microplate 100, 200 described above except for the differences explicitly noted herein. In particular, after the seeding and incubation of the cells contained within the plurality of microcavities 308 of wells 304, the plurality of wells 304 are flooded with a liquid culture medium such that the spheroids and/or organoids developed therein are submerged with the liquid culture medium. Plate lid 320 is thereafter reassembled onto microplate 300 and the assembly of plate lid 320 and microplate 300 is connected to a fluidic apparatus 330, as seen in FIG. 18. In this instance, access to the plurality of wells 304 is provided through the plurality of ports 324 of plate lid 320. With the assembly of microplate 300 and plate lid 320 coupled to fluidic apparatus 330, fluidic apparatus 330 establishes fluid communication with the plurality of wells 304 through the plurality of ports 324 of plate lid 320. Generally, fluidic apparatus 430 is configured to perfuse the plurality of wells 304 of microplate 300 and the plurality of fluid flow channels 326 of plate lid 320 with a liquid to thereby expose the spheroids and/or organoids included therein to a shear force.

In particular, fluidic apparatus 330 comprises a series of external fluid sources 332, a fluid distribution device 334, and an external fluid reservoir 340. External fluid sources 332 are media formulations that vary from one another and include a formulation that is specific to the tissue/organ model needs for the particular row of wells 304 that the respective external fluid source 332 is coupled to. In other words, each row of the plurality of wells 304 on microplate 300 is set to receive a different media formulation from a respective external fluid source 332 that is coupled to that particular row of wells 304. This is provided by the coupling of plate lid 320 to microplate 300, which includes a plurality of fluid flow channels 326 extending laterally in four respective rows. Each external fluid source 332 is coupled to fluid distribution device 334 via a conduit 336 disposed therebetween thereby establishing fluid communication between external fluid sources 332 and fluid distribution device 334. In the present example, fluid external sources 332 are pressurized media bags containing a particular media formulation fluid therein and fluid distribution device 334 is a manifold including flow control valves for each fluid external source 332 coupled thereto. Alternatively, fluid distribution device 334 may comprises a pump configured to output the media formulation fluids from external fluid sources 332.

Fluid distribution device 334 is coupled to an incoming port 327 of the plurality of ports 324 that is aligned with the respective row of interconnected wells 304 on microplate 300. Fluid distribution device 334 is configured to selectively manage (i.e. controllably release) an amount and rate of fluid from each external fluid source 332 to incoming ports 327. Fluid distribution device 334 is coupled to the assembly of plate lid 320 and microplate 300 via a series of tubes 338 extending between fluid distribution device 334 and the plurality of incoming ports 327. Each tube 338 is coupled to a particular conduit 336 that corresponds to the external fluid source 332 that includes the specific media formulation fluid that is intended to be delivered to the column of wells 304 that tube 338 is in fluid communication with. Upon the fluid reaching incoming ports 327, the fluid enters a first well 304 of the interconnected row of wells 304 thereby exposing the cell culture substrate of wells to the fluid flow such that the cells and the liquid medium stored within microcavities 308 are perfused by that specific media formulation transferring therethrough. The fluid is transferred through the other plurality of wells 304 that are interconnected with the first well 304 via the plurality of fluid flow channels 306 connecting the first well 304 with the remaining plurality of wells 304. As the fluid travels through the plurality of wells 304 the flow generates a shear force that effectively differentiates the cell culture substrate of wells 304.

Once the fluid reaches the last well 304 in the linear row of wells 304, the fluid is transferred out of microplate 300 via a respective outgoing port 328 that is aligned with the last well 304 of each interconnected row of wells 304. In this instance, each outgoing port 328 is coupled to a tube 338 that is coupled to plate lid 324 at external surface 322 at one end and to external fluid reservoir 340 at an opposite end. External fluid reservoir 340 collects the circulated fluid from microplate 300 for storage and subsequent discarding Subsequently, the assembly of microplate 300 and plate lid 320 may be disconnected from fluidic apparatus 330 to thereby allow plate lid 320 to be disassembled from microplate 300. In this instance, a different plate lid may be coupled to microplate 300, such as plate lid 420. Accordingly, the plurality of wells 304 of microplate 300 are no longer in fluid communication with adjacent wells 304 along a linear row, rather due to the orientation of the plurality of fluid flow channels 426 of plate lid 420 the plurality of wells 304 of microplate 300 are now in longitudinal communication with vertically adjacent wells 304.

Accordingly, the assembly of microplate 300 and plate lid 420 is coupled to fluidic apparatus 330 such that each column of wells 304 of microplate 300 is in fluid communication with a particular media formulation fluid contained with a respective external fluid source 332. Perfusing the columns of the plurality of wells 304 with the fluid contained within external fluid source 332 aids in cell differentiation and maturation of organoids due to the varying combinations of media formulation transferred into each respective well 304. The particular media formulation fluid that is coupled to the respective column of wells 304 depends on the particular assay condition intended to be applied within the respective wells 304. By inducing a varied fluid flow along the spheroids formed within the plurality of wells 304, the 3D cell aggregates grown within the plurality of wells 604 develop differentiated functions. By exposing the organoids in each well 304 to a different combination of fluid, the organoids are exposed to varying soluble factors that can encourage differentiated maturation, which further aids in forming organoids that closely simulate a functional representation of human organs. The adjustability of the particular plate lid 320, 420 assembled onto microplate 300 allows for the variation of fluid combinations that may be transferred to the plurality of wells 304.

The above-described fluidic devices, in particular the microplates, include multiple wells interconnected with one another by multiple fluid flow channels positioned therebetween a respective pair of adjacent wells. The multiple wells each including a microcavity substrate that is sized and shaped to receive cells therein for development of organoids. The multiple channels are sized and shaped to allow for a fluid to flow through the multiple wells to thereby generate a shear force along the microcavity substrates of each well. Based on the foregoing, it should be understood that the fluidic apparatuses described herein may be coupled to the microplate and plate lid to thereby generate the shear force within the microplate and provide for the development, maturation, and differentiation of the organoids/spheroids contained therein.

It will be apparent to those skilled in the art that various modifications and variations can be made to the embodiments described herein without departing from the spirit and scope of the claimed subject matter. Thus it is intended that the specification cover the modifications and variations of the various embodiments described herein provided such modification and variations come within the scope of the appended claims and their equivalents.

What is claimed is:

1. A fluidic device for culturing cells, comprising:
   (a) a microplate comprising multiple wells and multiple channels, wherein the channels extend between the wells such that the channels interconnect the wells; and
   (b) a plate lid that releasably engages the microplate to thereby enclose the wells and the channels, wherein the plate lid includes multiple ports extending therethrough, wherein the ports are sized and shaped to align with the wells when the plate lid is engaged with the microplate;
   wherein the wells include a culture surface such that a cell culture medium received therein is deposited over the culture surface;
   wherein at least one channel that extends between adjacent ones of the wells is spaced from the culture surfaces of the adjacent wells defining a gap between the at least one channel and the culture surfaces of the adjacent wells for collection of the cell culture medium, the gap being configured to partially store and/or maintain the cell culture medium received within the well.

2. The fluidic device of claim 1, wherein the channels are sized to facilitate circulation of the medium across the multiple wells to thereby generate a shear force along the culture surfaces.

3. The fluidic device of claim 1, wherein the channels include a sidewall extending between the wells, wherein the sidewalls are sized to partially retain the cell culture medium within the channels.

4. The fluidic device of claim 1, wherein the culture surface comprises a gas permeable microcavity substrate.

5. The fluidic device of claim 1, wherein a first portion of each of the multiple ports are configured to transfer fluid from an external fluid source to the wells for circulation, wherein a second portion of each of the multiple ports are configured to transfer circulated fluid from the wells to an external reservoir.

6. The fluidic device of claim 5, wherein the plate lid includes an elastomer lining along a bottom surface that forms a seal between the plate lid and the microplate.

7. The fluidic device of claim 6, wherein the elastomer lining forms a septum between the plate lid and the microplate, and wherein the elastomer lining is capable of being punctured such that the puncturable elastomer lining is punctured through to establish fluid communication between the microplate and the external fluid source.

8. The fluidic device of claim 1, further comprising a fastening mechanism configured to securely attach the plate lid to the microplate.

9. The fluidic device of claim 1, further comprising an insert having a plurality of microwells positioned within the multiple wells.

10. The fluidic device of claim 9, wherein the plurality of microwells of the insert comprise a porous membrane.

11. The fluidic device of claim 9, wherein the wells are shaped to form a flat bottom surface, wherein the plurality of microwells are shaped to form a microcavity bottom surface, wherein the flat bottom surface of the wells is configured to receive the microcavity bottom surface of the plurality of microwells.

12. The fluidic device of claim 9, wherein the wells are shaped to form a microcavity bottom surface, wherein the plurality of microwells are shaped to form a flat bottom surface, wherein the microcavity bottom surface of the wells is configured to receive the flat bottom surface of the plurality of microwells.

13. The fluidic device of claim 9, wherein the wells and the plurality of microwells are similarly shaped to form a microcavity bottom surface such that the microcavity bottom surface of the plurality of microwells is sized and shaped to fit within the microcavity bottom surface of the wells.

14. A fluidic apparatus for culturing cells, comprising:
(a) a microplate comprising multiple wells and multiple channels, wherein the channels extend between the wells such that the channels interconnect the wells, wherein the wells include a culture surface that cultivates cells therein;
(b) a plate lid that releasably engages the microplate to thereby enclose the wells and the channels, wherein the plate lid includes multiple ports extending therethrough, wherein the ports are sized and shaped to align with the wells when the plate lid is engaged with the microplate;
(c) an external fluid source coupled to at least one of the multiple ports such that the external fluid source transfers a cell culture medium to the wells of the microplate via the at least one port;
wherein at least one channel that extends between adjacent ones of the wells is spaced from the culture surfaces of the adjacent wells defining a gap between the at least one channel and the culture surfaces of the adjacent wells for collection of the cell culture medium, the gap being configured to partially store and/or maintain the cell culture medium received within the well.

15. The fluidic apparatus of claim 14, wherein the channels are sized to facilitate circulation of the fluid from the external fluid source across the wells to thereby generate a shear force along the culture surfaces.

16. The fluidic apparatus of claim 14, wherein the external fluid source is in fluid communication with the port via a manifold, wherein the manifold comprises a control valve configured to control a flow of the cell culture medium transferred from the external fluid source to the multiple wells.

17. The fluidic apparatus of claim 14, wherein the external fluid source is in fluid communication with the port via a pump, wherein the pump is configured to control a flow of the cell culture medium transferred from the external fluid source to the multiple wells.

18. The fluidic apparatus of claim 14, further comprising an insert having a plurality of microwells that are sized and shaped in accordance with the wells such that the wells are configured to receive the plurality of microwells therein, wherein the insert cultivates an organoid within the plurality of microwells, wherein the insert comprises a porous membrane such that the organoid is in fluid communication with the culture surface of the wells.

19. The fluidic apparatus of claim 15, wherein each channel includes a pair of sidewalls extending along each well such that the sidewalls partially retain the circulated cell culture medium and cells within the channels.

20. A fluidic device for culturing cells, comprising:
(a) a microplate comprising multiple wells; and
(b) a plate lid comprising multiple channels, wherein the plate lid releasably engages the microplate to enclose the wells such that the channels are aligned to extend between the wells, and wherein the plate lid includes multiple ports extending therethrough, wherein the ports are sized and shaped to align with the wells when the plate lid is engaged with the microplate;
wherein the wells include a culture surface such that a cell culture medium received therein is deposited over the culture surface;
wherein at least one channel that extends between adjacent ones of the wells interconnects the wells for communication of the cell culture medium between the culture surfaces of the adjacent wells.

21. The fluidic device of claim 20, wherein the plate lid includes an elastomer lining along a bottom surface that forms a seal between the plate lid and the microplate.

22. The fluidic device of claim 21, wherein the elastomer lining forms a septum between the plate lid and the microplate, and wherein the elastomer lining is capable of being punctured such that the puncturable elastomer lining is punctured through to establish fluid communication to the microplate through the plate lid.

23. The fluidic device of claim 21, wherein the multiple channels are formed within the elastomer lining, wherein the multiple channels extend laterally across the bottom surface thereby forming linear rows of multiple channels.

24. The fluidic device of claim 21, wherein the multiple channels are formed within the elastomer lining, wherein the multiple channels extend longitudinally across the bottom surface thereby forming linear columns of multiple channels.

25. The fluidic device of claim 21, wherein the elastomer lining is configured to form an individual seal around each well of the multiple wells when the plate lid is releasably engaged to the microplate.

* * * * *